(12) United States Patent
Miller et al.

(10) Patent No.: US 7,547,879 B2
(45) Date of Patent: *Jun. 16, 2009

(54) LONGITUDINAL FIELD DRIVEN ION MOBILITY FILTER AND DETECTION SYSTEM

(75) Inventors: Raanan A. Miller, Chestnut Hill, MA (US); Markus Zahn, Lexington, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 362 days.

This patent is subject to a terminal disclaimer.

(21) Appl. No.: 11/404,215

(22) Filed: Apr. 14, 2006

(65) Prior Publication Data

US 2006/0192102 A1    Aug. 31, 2006

Related U.S. Application Data

(63) Continuation of application No. 10/887,016, filed on Jul. 8, 2004, now Pat. No. 7,456,390, which is a continuation of application No. 10/082,803, filed on Feb. 21, 2002, now Pat. No. 6,815,669, which is a continuation-in-part of application No. 09/439,543, filed on Nov. 12, 1999, now Pat. No. 6,512,224, which is a continuation-in-part of application No. 09/358,312, filed on Jul. 21, 1999, now Pat. No. 6,495,823.

(51) Int. Cl.
    *H01J 49/40*      (2006.01)

(52) U.S. Cl. ............... 250/286; 250/288; 250/294; 250/290; 250/287; 250/291; 250/281; 250/282

(58) Field of Classification Search ............... 250/288, 250/286, 294, 290, 287, 291, 281, 282
See application file for complete search history.

(56) References Cited

U.S. PATENT DOCUMENTS

| | | |
|---|---|---|
| 2,615,135 A | 10/1952 | Glenn |
| 2,818,507 A | 12/1957 | Britten |
| 2,919,348 A | 12/1959 | Bierman |
| 3,511,986 A | 5/1970 | Llewellyn |
| 3,619,605 A | 11/1971 | Cook et al. |
| 3,621,240 A | 11/1971 | Cohen et al. |
| 3,648,046 A | 3/1972 | Denison et al. |
| 3,931,589 A | 1/1976 | Aisenberg et al. |

(Continued)

FOREIGN PATENT DOCUMENTS

SU      966583 A      10/1982

(Continued)

OTHER PUBLICATIONS

"Advanced Cross-Enterprise Technology Development for NASA Missions," Revised NASA Research Announcement NRA99-OSS-05 pp. 1-C19 (1999).

(Continued)

*Primary Examiner*—Jack I Berman
*Assistant Examiner*—Meenakshi S Sahu
(74) *Attorney, Agent, or Firm*—Ropes & Gray LLP

(57) ABSTRACT

An asymmetric field ion mobility spectrometer for filtering ions via an asymmetric electric field, an ion flow generator propulsing ions to the filter via a propulsion field.

61 Claims, 20 Drawing Sheets

U.S. PATENT DOCUMENTS

| | | | |
|---|---|---|---|
| 4,019,989 | A | 4/1977 | Hazewindus et al. |
| 4,025,818 | A | 5/1977 | Giguere et al. |
| 4,136,280 | A | 1/1979 | Hunt et al. |
| 4,163,151 | A | 7/1979 | Bayless et al. |
| 4,167,668 | A | 9/1979 | Mourier |
| 4,201,921 | A | 5/1980 | McCorkle |
| 4,315,153 | A | 2/1982 | Vahrenkamp |
| 4,517,462 | A | 5/1985 | Boyer et al. |
| 4,761,545 | A | 8/1988 | Marshall et al. |
| 4,885,500 | A | 12/1989 | Hansen et al. |
| 4,931,640 | A | 6/1990 | Marshall et al. |
| 5,019,706 | A | 5/1991 | Alleman et al. |
| 5,047,723 | A | 9/1991 | Puumalainen |
| 5,144,127 | A | 9/1992 | Williams et al. |
| 5,298,745 | A | 3/1994 | Kernan et al. |
| 5,373,157 | A | 12/1994 | Hiroki et al. |
| 5,420,424 | A | 5/1995 | Carnahan et al. |
| 5,492,867 | A | 2/1996 | Kotvas et al. |
| 5,536,939 | A | 7/1996 | Freidhoff et al. |
| 5,541,408 | A | 7/1996 | Sittler |
| 5,644,131 | A | 7/1997 | Hansen |
| 5,654,544 | A | 8/1997 | Dresch |
| 5,723,861 | A | 3/1998 | Carnahan et al. |
| 5,736,739 | A | 4/1998 | Uber et al. |
| 5,789,745 | A | 8/1998 | Martin et al. |
| 5,801,379 | A | 9/1998 | Kouznetsov |
| 5,811,059 | A | 9/1998 | Genovese et al. |
| 5,834,771 | A | 11/1998 | Yoon et al. |
| 5,838,003 | A | 11/1998 | Bertsch et al. |
| 5,852,302 | A | 12/1998 | Hiraishi et al. |
| 5,869,344 | A | 2/1999 | Linforth et al. |
| 5,965,882 | A | 10/1999 | Megerle et al. |
| 6,049,052 | A | 4/2000 | Chutjian et al. |
| 6,051,832 | A | 4/2000 | Bradshaw |
| 6,066,848 | A | 5/2000 | Kassel et al. |
| 6,107,628 | A | 8/2000 | Smith et al. |
| 6,124,592 | A | 9/2000 | Spangler |
| 6,157,029 | A | 12/2000 | Chutjian et al. |
| 6,157,031 | A | 12/2000 | Prestage |
| 6,188,067 | B1 | 2/2001 | Chutjian et al. |
| 6,200,539 | B1 | 3/2001 | Sherman et al. |
| 6,262,416 | B1 | 7/2001 | Chutjian et al. |
| 6,281,494 | B1 | 8/2001 | Chutjian et al. |
| 6,323,482 | B1 | 11/2001 | Clemmer et al. |
| 6,495,823 | B1 | 12/2002 | Miller et al. |
| 6,504,149 | B2 | 1/2003 | Guevremont et al. |
| 6,509,562 | B1 | 1/2003 | Yang et al. |
| 6,618,712 | B1 | 9/2003 | Parker et al. |
| 6,621,077 | B1 | 9/2003 | Guevremont et al. |
| 6,815,669 | B1 * | 11/2004 | Miller et al. ............... 250/286 |
| 7,456,390 | B2 * | 11/2008 | Miller et al. ............... 250/287 |
| 2001/0030285 | A1 | 10/2001 | Miller et al. |
| 2002/0070338 | A1 | 6/2002 | Loboda |
| 2002/0134932 | A1 | 9/2002 | Guevremont et al. |
| 2003/0089847 | A1 | 5/2003 | Guevremont et al. |

FOREIGN PATENT DOCUMENTS

| | | | |
|---|---|---|---|
| SU | 1337934 | A2 | 9/1987 |
| SU | 1627984 | A2 | 2/1991 |
| SU | 1405489 | | 6/1998 |
| SU | 1412447 | A1 | 6/1998 |
| SU | 1485808 | A1 | 6/1998 |
| WO | WO-96/19822 | A1 | 6/1996 |
| WO | WO-97/38302 | | 10/1997 |
| WO | WO-99/21212 | | 4/1999 |
| WO | WO-00/08454 | | 2/2000 |
| WO | WO-00/08455 | | 2/2000 |
| WO | WO-00/08456 | | 2/2000 |
| WO | WO-00/08457 | | 2/2000 |
| WO | WO-01/08197 | A1 | 2/2001 |
| WO | WO-01/22049 | A2 | 3/2001 |
| WO | WO-01/35441 | A1 | 5/2001 |
| WO | WO-01/69220 | A2 | 9/2001 |
| WO | WO-01/69647 | A2 | 9/2001 |
| WO | WO-02/071053 | A2 | 9/2002 |

OTHER PUBLICATIONS

Raizer et al., "Radio-frequency capacitive discharges," CRC Press pp. 1-3 (1995).

Guevremont et al., "Atmospheric pressure ion focusing in a high-field asymmetric waveform ion mobility spectrometer," Review of Scientific Instruments 70:2:1370-1383.

Buryakov, et al., "Separation of Ions According to Mobility in A Strong AC Electric Field," Letters to Journal of Technical Physics, 17:11-12 (1991).

Carnahan, B., et al., "Field Ion Spectrometry—A New Technology for Cocaine and Heroin Detection," SPIE, 2937:106-119 (1997).

Guevremont, R., et al., "Calculation of Ion Mobilities From Electrospray Ionization High-Field Asymmetric Waveform Ion Mobility Spectrometry Mass Spectrometry," Journal of Chemical Physics, 114(23):10270-10277 (2001).

"A Micromachined Field Driven Radio Frequency-Ion Mobility Spectrometer for Trace Level Chemical Detection," A Draper Laboratory Proposal Against the "Advanced Cross-Enterprise Technology Development for NASA Missions," Solicitation, NASA NRA 99-OSS-05.

Carnahan, B., et al., "Field Ion Spectrometry—A New Analytical Technology for Trace Gas Analysis," ISA Paper 96-009:87-96 (1996).

Verenchikov, A.N., et al., Analysis ions in solutes by gaseous ion analyzer. "Chemical Analysis of the Environmental Objects," red. Malakhov. Novosibirsk, Nauka, pp. 127-134 (1991).

Buryakov et al., "Drift Spectrometer for the Control of Amine Traces in the Atmosphere," J. Analytical Chem. 48(1):156-165 (1993).

Guevremont et al., "High Field Asymmetric Waveform Ion Mobility Spectrometry-Mass Spectrometry: An Investigation of Leucine Enkephalin Ions Produced by Electrospray Ionization," J. Am. Soc. Mass. Spectrom. 10:492-501 (1999).

Handy et al., "Determination of Nanomolar Levels of Perchlorate in Water by ESI-FAIMS-MS," JAAS 15:907-911 (2000).

Buryakov et al., Devices and Methods of the Gaseous Electrophoresis. "Chemical Analysis of the Environmental Objects," red. Malakhov. Novosibirsk, Nauka, pp. 113-127 (1991).

Krylov, "A Method of Reducing Diffusion Losses in a Drift Spectrometer," Technical Physics, 44(1):113-116.

Riegner et al., "Qualitative Evaluation of Field Ion Spectrometry for Chemical Warfare Agent Detection," Proceedings of the ASMS Conference on Mass Spectrometry and allied Topics, pp. 473A-473B (1997).

Barnet et al., "Isotope Separation Using High-Field Asymmetric Waveform Ion Mobility Spectrometry," Nuclear Instruments & Methods in Physics Research, 450(1):179-185 (2000).

Pilzecker et al., "On-Site Investigations of Gas Insulated Substations Using Ion Mobility Spectrometry for Remote Sensing of SF6 Decomposition," IEEE, pp. 400-403 (2000).

Krylov, "Pulses of Special Shapes Formed on a Capacitive Load," Instruments and Experimental Techniques, 40(5):628 (1997).

Buryakov, I.A., et al., "A New Method of Separation of Multi-atomic Ions by Mobility at Atmospheric Pressure Using a High-Frequency Amplitude-Asymmetric Strong Electric Field," Int. Journal of Mass. Spectrometry and Ion Processes V. 128, pp. 143-148, (1993).

Miller et al., "A Novel Micromachined High-Field Asymmetric Waveform-Ion Mobility Spectrometer," Sensors and Actuators B, vol. B67, No. 3, pp. 300-306 (2000).

* cited by examiner

US 7,547,879 B2

LONGITUDINAL FIELD DRIVEN ION MOBILITY FILTER AND DETECTION SYSTEM

REFERENCE TO RELATED APPLICATIONS

This application is a Continuation of U.S. patent application Ser. No. 10/887,016, filed on Jul. 8, 2004, which is a Continuation of U.S. patent application Ser. No. 10/082,803, filed on Feb. 21, 2002, now U.S. Pat. No. 6,815,669, which is a Continuation-In-Part of U.S. application Ser. No. 09/439,543, filed on Nov. 12, 1999, now U.S. Pat. No. 6,512,224, which is a Continuation-In-Part of U.S. application Ser. No. 09/358,312, filed on Jul. 21, 1999, now U.S. Pat. No. 6,495,823, all of which are incorporated herein by reference.

FIELD OF THE INVENTION

The present invention relates to chemical analytical systems based on ion mobility, and conveyance of ions through such a system.

BACKGROUND OF THE INVENTION

The ability to detect and identify explosives, drugs, chemical and biological agents as well as monitor air quality has become increasingly more critical given increasing terrorist and military activities and environmental concerns. Previous detection of such agents was accomplished with conventional mass spectrometers, time of flight ion mobility spectrometers and conventional field asymmetric ion mobility spectrometers (FAIMS).

Mass spectrometers are very sensitive and selective with fast response time. Mass spectrometers, however, are large and require significant amounts of power to operate. They also require a powerful vacuum pump to maintain a high vacuum in order to reduce ion neutral interactions and permit detection of the selected ions. Mass spectrometers are also very expensive.

Another spectrometric technique which is less complex is time of flight ion mobility spectrometry which is the method currently implemented in most portable chemical weapons and explosives detectors. The detection is based not solely on mass, but on charge and cross-section of the molecule as well. However, because of these different characteristics, molecular species identification is not as conclusive and accurate as the mass spectrometer. Time of flight ion mobility spectrometers typically have unacceptable resolution and sensitivity limitations when attempting to reduce their size. In time of flight ion mobility, the resolution is proportional to the length of the drift tube. The longer the tube the better the resolution, provided the drift tube is also wide enough to prevent all ions from being lost to the side walls due to diffusion. Thus, fundamentally, miniaturization of time of flight ion mobility systems leads to a degradation in system performance. While conventional time of flight devices are relatively inexpensive and reliable, they suffer from several limitations. First, the sample volume through the detector is small, so to increase spectrometer sensitivity either the detector electronics must have extremely high sensitivity, requiring expensive electronics, or a concentrator is required, adding to system complexity. In addition, a gate and gating electronics are usually needed to control the injection of ions into the drift tube.

FAIMS spectrometry was developed in the former Soviet Union in the 1980's. FAIMS spectrometry allows a selected ion to pass through a filter while blocking the passage of undesirable ions. But the only commercial prior art FAIMS spectrometer was large and expensive, e.g., the entire device was nearly a cubic foot in size and cost over $25,000. Such systems are not suitable for use in applications requiring small detectors. They are also relatively slow, taking as much as one minute to produce a complete spectrum of the sample gas, are difficult to manufacture and are not mass producible.

The prior art FAIMS devices depend upon a carrier gas that flows in the same direction as the ion travel through the filter. However, the pumps required to draw the sample medium into the spectrometer and to provide a carrier gas can be rather large and can consume large amounts of power.

It is therefore an object of the present invention to provide an ion filter and detection system which does not require the high flow rate, high power consumption pumps normally associated with FAIMS spectrometers.

It is another object of the present invention to provide method and apparatus for highly efficient conveyance of ions into and through a high field ion mobility filter.

It is a further object of the present invention to provide method and apparatus for efficient conveyance of ions into and through a high field ion mobility filter without the use of a carrier gas.

It is another object of the present invention to provide a FAIMS filter and detection system which can quickly and accurately control the flow of selected ions to produce a sample spectrum.

It is a further object of the present invention to provide a FAIMS filter and detection system which has a sensitivity of parts per billion to parts per trillion.

It is a further object of the present invention to provide a FAIMS filter and detection system which may be packaged in a single chip.

It is a further object of the present invention to provide a FAIMS filter and detection system which is cost effective to implement, produce and operate.

SUMMARY OF THE INVENTION

The present invention features an ion mobility spectrometer for filtering ions via an asymmetric electric field. Ions are transported along the longitudinal ion flow path via an ion flow generator. The ion flow generator preferably provides ion propulsion via a local electric field in the flow path. Operation of the invention enables elimination or reduction of flow rate and power requirements of conventional gas flow.

In a preferred embodiment, a longitudinal electric field generated by the ion flow generator propels ionized sample received from an ionization region through a compensated, asymmetric electric field of the ion filter, with a desired species passing through the filter and flowing toward a detector region. Various options are possible. In one embodiment, a low volume gas flow carries the sample to the filter. In other embodiment, there is no need for gas flow and ion steering, or the longitudinal field itself, propels ions into the filter region, where the ions are further propelled by the ion flow generator.

In another embodiment, a supply of clean filtered air is flowed in the negative longitudinal direction opposite the desired direction of ion flow to keep the ion filter and detector regions free of neutrals and to help remove solvent, reduce clustering, and minimize the effects of humidity.

A preferred embodiment of the present invention features an ion mobility spectrometer having a housing structure that defines a flow path (also known as a drift tube) that begins at a sample inlet for receipt of sample (i.e., sample molecules to be analyzed) and brings the sample to an ionization region. Once ionized, the sample passes to the ion filter, with desired ion species passing through the filter in the flow path, as propelled by the ion flow generator.

In one embodiment, the ion filter is provided with a plurality of high frequency, high voltage filter electrodes for creation of the asymmetric electric field transverse to the longitudinal ion flow direction along the flow path. In a preferred embodiment, this field is compensated, to pass only a desired ion species for downstream detection. In another embodiment, filtering is trajectory based without requiring compensation.

The ion flow generator creates a longitudinal electric field along the flow path (transverse to the asymmetric electric field) for propelling or transporting the ions through the asymmetric electric field toward the output region to enable detection and analysis. The ionization source may include a radiation source, an ultraviolet lamp, a corona discharge device, electrospray nozzle, plasma source, or the like.

In one embodiment, an electric controller supplies a compensation bias and an asymmetric periodic voltage to the ion filter. The ion filter typically includes a pair of spaced electrodes for creating the asymmetric electric field between the electrodes. The ion flow generator typically includes a plurality of spaced discrete electrodes proximate to the filter electrodes for creating a longitudinal direction electric field which propels the ions through the transverse asymmetric electric field, and onward for detection. The ion filter and flow generator may share none, some or all electrodes.

In another embodiment, the ion flow generator includes spaced resistive layers and a voltage is applied along each layer to create the longitudinally directed electric field which propels the ions through the filter's compensated asymmetric electric field and to the detector.

In another embodiment, the ion filter includes a first plurality of discrete electrodes electrically connected to an electric controller which applies the asymmetric periodic voltage to them. The ion flow generator includes a second plurality of discrete electrodes dispersed among the electrodes of the ion filter and connected to a voltage source which applies a potential gradient along the second plurality of discrete electrodes. Compensation voltage applied to the filter opens the filter to pass a desired ion species if present in the sample. If the compensation voltage is scanned, then a complete spectrum of the compounds in a sample can be gathered.

In one embodiment, the ion filter includes electrodes on an inside surface of the housing and the ion flow generator includes electrodes proximate to the ion filter electrodes. The housing may be formed using planar substrates. The ion detector also includes electrodes on an inside surface of the housing proximate to the ion filter and the ion flow generator.

In another embodiment, the ion filter may include electrodes on an outside surface of the housing and the ion flow generator then includes resistive layers on an inside surface of the housing. A voltage is applied along each resistive layer to create a longitudinal electric field. Alternatively, the ion-filter and the ion flow generator are combined and include a series of discrete conductive elements each excited by a voltage source at a different phase.

In another embodiment, both the longitudinal and transverse fields and voltages are applied or generated via the same electrodes or via members of a set of electrodes. Because of the flexibility of the electronic drive system of the invention, all or part of the electrode set may be used for a given function or more than one function in series or simultaneously.

In yet a further embodiment of the invention, filtering is achieved without compensation of the filter field. In one practice, the spectrometer has a single RF (high frequency, high voltage) filter electrode on a first substrate, and a plurality of multi-function electrodes on a second substrate that are formed facing the filter electrode over the flow path. The plurality of electrodes forms a segmented detector electrode. Ions are filtered and detected by trajectory, being controlled by the asymmetric field and landing on an appropriate one of the detector electrode segments. Thus filtering is achieved without compensation of the filter field in a very compact package. The detector electrodes are monitored, wherein a particular species can be identified based on its trajectory for a given detection and given knowledge of the signals applied, the fields generated, and the transport (whether gas or electric field).

In practice of the invention, prior art pumps used to draw a sample, such as a gas containing compounds to be analyzed, into a FAIMS spectrometer, and to provide a flow of carrier gas, can be made smaller or even eliminated in practice of the invention. This is enabled in practice of the invention by incorporation of an ion flow generator which creates a longitudinal electric field in the direction of the intended ion travel path to propel the ions toward a detector region after passing through a transversely directed asymmetric electric field which acts as an ion filter.

The result is the ability to incorporate lower cost, lower flow rate, and smaller, even micromachined pumps, in embodiments of the invention; a decrease in power usage; the ability to apply clean filtered gas (e.g., dehumidified air) in a direction opposite the direction of ion travel to eliminate ion clustering and the sensitivity of the spectrometer to humidity. Separate flow paths for the source gas and the clean filtered gas may not be required, thus reducing the structure used to maintain separate flow paths taught by the prior art. Moreover, if an electrospray nozzle is used as the ionization source, the electrodes used to create the fine droplets of solvent can be eliminated because the electrodes which create the longitudinal and transverse electric fields can be used to function both to transport the ions and to create the fine spray of solvent droplets.

In a practice of the invention, an extremely small, accurate and fast FAIMS filter and detection system can be achieved by defining an enclosed flow path between a sample inlet and an outlet using a pair of spaced substrates and disposing an ion filter within the flow path, the filter including a pair of spaced electrodes, one electrode associated with each substrate and a controller for selectively applying a bias voltage and an asymmetric periodic voltage across the electrodes to control the path of ions through the filter. In a further embodiment of the invention, it is possible to provide an array of filters to detect multiple selected ion species.

Alternative filter field compensation in practice of embodiments of the invention may be achieved by varying the duty cycle of the periodic voltage, with or without a bias voltage. Furthermore, in an embodiment of the invention, it is possible that by segmenting the detector, ion detection may be achieved with greater accuracy and resolution by detecting ions spatially according to the ions' trajectories as the ions exit the filter.

It will be further understood that while ion travel within the ion filter is determined by the compensated asymmetric filter field and the ion transport field, the invention may also include an ion concentrating feature for urging ions toward the center of the flow path. In one embodiment this concentrating is achieved where fields between electrodes on each substrate work together to urge the ions toward the center of the flow path as they pass there between approaching the ion filter.

In other embodiments, ion filtering is achieved without the need for compensation of the filter field. In one illustrative embodiment, a spectrometer of the invention has preferably a single RF (high frequency, high voltage) filter electrode. A segmented filter-detector electrode set faces the first electrode over the flow path, with the filter-detector electrode set having a plurality of electrodes in a row maintained at virtual ground. The asymmetric field signal is applied to the filter electrode and the asymmetric field is generated between the filter electrode and the filter-detector electrode set. Ions flow in the alternating asymmetric electric field and travel in oscillating paths that are vectored toward collision with a filter electrode, and in absence of compensation, favorably enables driving of the ions to various electrodes of the filter-detector electrode set. These collisions are monitored.

In a further embodiment, upstream biasing effects which ions flow to the filter. For example, a sample flows into an ionization region subject to ionization source, and electrodes are biased to deflect and affect flow of the resulting ions. Positive bias on a deflection electrode repels positive ions toward the filter and attracting electrodes being negatively biased attract the positive ions into the central flow of the ion filter, while negative ions are neutralized on the deflection electrode and which are then swept out of the device. Negative bias on the deflection electrode repels negative ions toward the filter and attracting electrodes positively biased attract the negative ions into the central flow path of the filter, while positive ions are neutralized on the deflection electrode.

In an embodiment, the path taken by a particular ion in the filter is mostly a function of ion size, cross-section and charge, which will determine which of the electrodes of the filter-detector electrode set that a particular ion species will drive into. This species identification also reflects the polarity of the ions and the high/low field mobility differences ("alpha") of those ions. Thus a particular ion species can be identified based on its trajectory (i.e., which electrode is hit) and knowledge of the signals applied, the fields generated, and the transport characteristics (such as whether gas or electric field).

In practice of the filter function of the invention, where the upstream biasing admits positive ions into the filter, those positive ions with an alpha less than zero will have a mobility decrease with an increase of a positively offset applied RF field. This will affect the trajectory of these ions toward the downstream detector electrodes. However, a positive ion with an alpha greater than zero will have a mobility increase with an increase of a negatively offset applied RF field, which in turn will shorten the ion trajectory toward the nearer detector electrodes. Similarly, where the filter received negative ions, a negative ion with an alpha less than zero will have a mobility increase with an increase of a positively offset applied RF field; this will tend to affect the ion trajectory toward the downstream detector electrodes. However, a negative ion with an alpha greater than zero will have a mobility increase with an increase of a negatively offset applied RF field, which in turn will tend to shorten the ion trajectory toward the nearer detector electrodes. Thus, ions can be both filtered and detected in a spectrometer of the invention without the need for compensation.

In various embodiments of the invention, a spectrometer is provided where a plurality of electrodes are used to create a filter field and a propulsion field, in a cooperative manner that may be feature simultaneous, iterative or interactive use of electrodes. Where a plurality of electrodes face each other over a flow path, the filter field and the propulsion field may be generated using the same or different members of the electrode plurality. This may be achieved in a simple and compact package.

In practice of the invention, a spectrometer is provided in various geometries where a plurality of electrodes are used to create a filter and a propulsion field, in a cooperative manner that may be simultaneous or interactive. Where a plurality of electrodes face each other over a flow path, the filter field and the propulsion field may be generated using the same or different members of the electrode plurality to pass selected ion species through the filter.

It will be appreciated that in various of the above embodiments, a spectrometer can be provided in any arbitrarily shaped geometry (planar, coaxial, concentric, cylindrical) wherein one or more sets of electrodes are used to create a filtering electric field for ion discrimination. The same or a second set of electrodes, which may include an insulative or resistive layer, are used to create an electric field at some angle to the filtering electric field for the purpose of propelling ions through the filtering field to augment or replace the need for pump-driven propulsion such as with a carrier gas.

It will now be appreciated that a compact FAIMS spectrometer has been provided with e-field ion propulsion. Benefits of the invention include provision of a stable, easily controlled ion flow rate without the need for gas flow regulation. Elimination of the need for gas flow regulation reduces complexity and cost and improves reliability. Dramatic reduction of gas flow substantially reduces power consumption. Operation of the invention can reduce the amount of sample neutrals entering the analysis region between the filter electrodes. If only ions are injected into the filter, then it is easier to keep the ion filter in a controlled operating state, such as control of moisture level. The result is very reproducible spectra in a low power analytical system.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

A preferred embodiment of the present invention provides method and apparatus for conveyance of ions in and through an ion filter without the need for a carrier gas in an ion-mobility-based analytical system. In embodiments of the present invention, the need for pumps is either eliminated or the pumps are made smaller, even micromachined. Furthermore, separate flow paths for the source gas and the carrier gas are not required. In one filter embodiment, filtered gas is introduced to flow in a direction opposite the direction of ion travel to eliminate ion clustering and to improve system sensitivity. Preferred and alternative embodiments of the invention are set forth below as an illustration and as a limitation.

Figure 1:
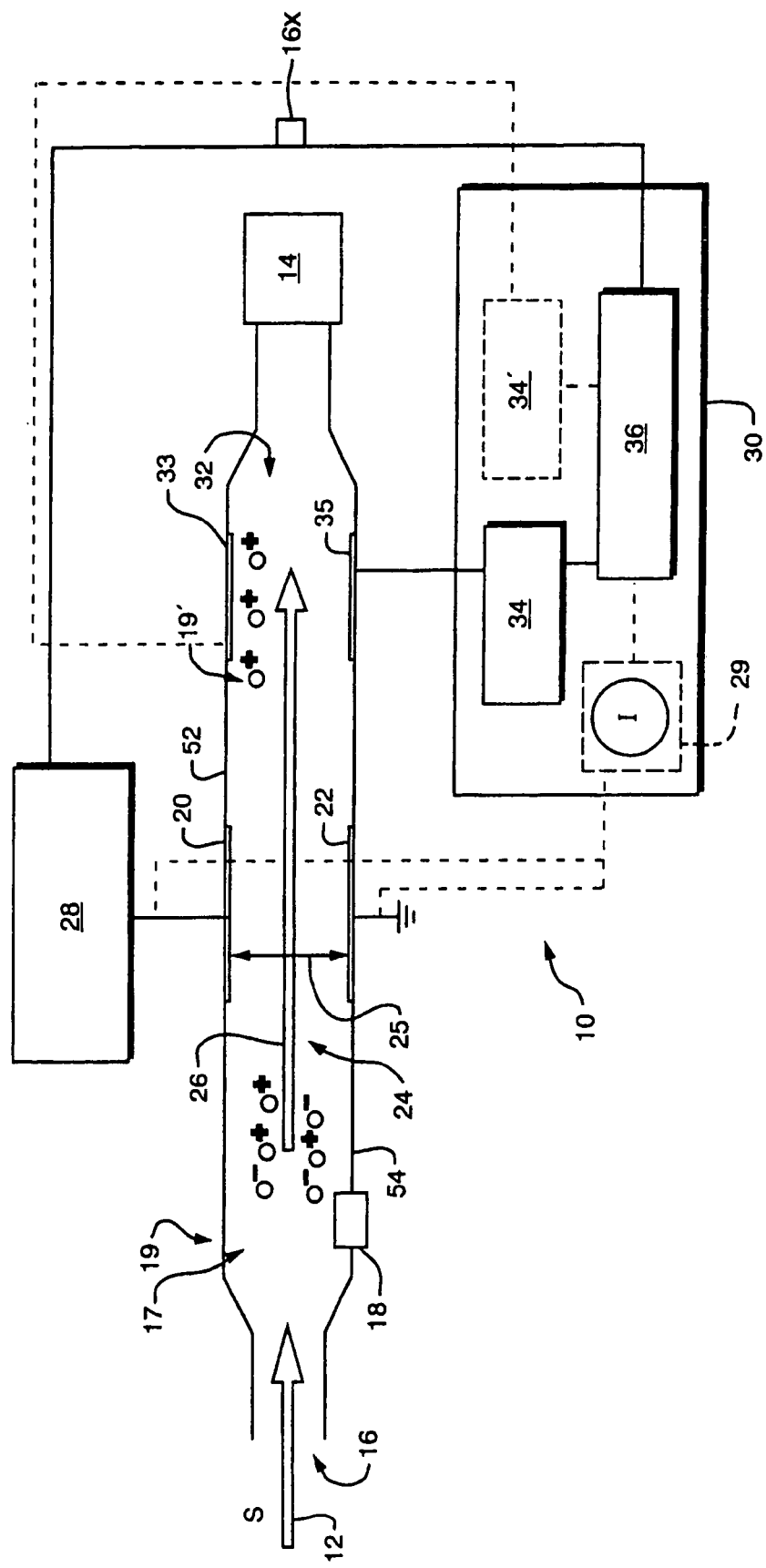
FIG. 1 is a schematic block diagram of a PFAIMS filter and detection system according to the present invention.

A preferred planar FAIMS (PFAIMS) spectrometer 10, FIG. 1, operates by drawing a carrier gas 12 containing a sample S to be analyzed (often collectively referred to as a gas sample), by means of pump 14, through inlet 16 and into ionization region 17. The gas sample is ionized by ionization source 18. Source 18 may include an ultraviolet light source, a radioactive device, plasma source, corona discharge device, electrospray head, or the like.

The ions 19 flow from the ionization region 17 along flow path 26 into filter 24 defined by facing electrodes 20 and 22. As these ions pass between electrodes 20 and 22 they are exposed to an asymmetric electric field 25 established between the filter electrodes, induced by a voltage applied from a source, such as voltage generator 28 directed by electronic controller 30. Filter field 25 is transverse to the longitudinal flow of gas and ions along flow path 26.

The system is preferably driven by electronic controller 30, which may include, for example, amplifier 34 and microprocessor 36. Amplifier 34 amplifies the output of detector 32, which is a function of the charge collected by electrode 35 and provides the output to microprocessor 36 for analysis. Similarly, amplifier 34', shown in phantom, may be provided where electrode 33 is also utilized as a detector.

As part of the FAIMS filtering function, some compensation must be applied to the filter; which in turn selects a particular ion species that will pass through the filter. In operation, as ions pass through filter field 25, some ions are neutralized as they travel into and collide with filter electrodes 20 and 22. However the filter field is compensated to bring a particular species of ion back toward the center of the flow path, preventing it from being neutralized. Thus a desired ion species 19' passes through the filter.

Figure 2:
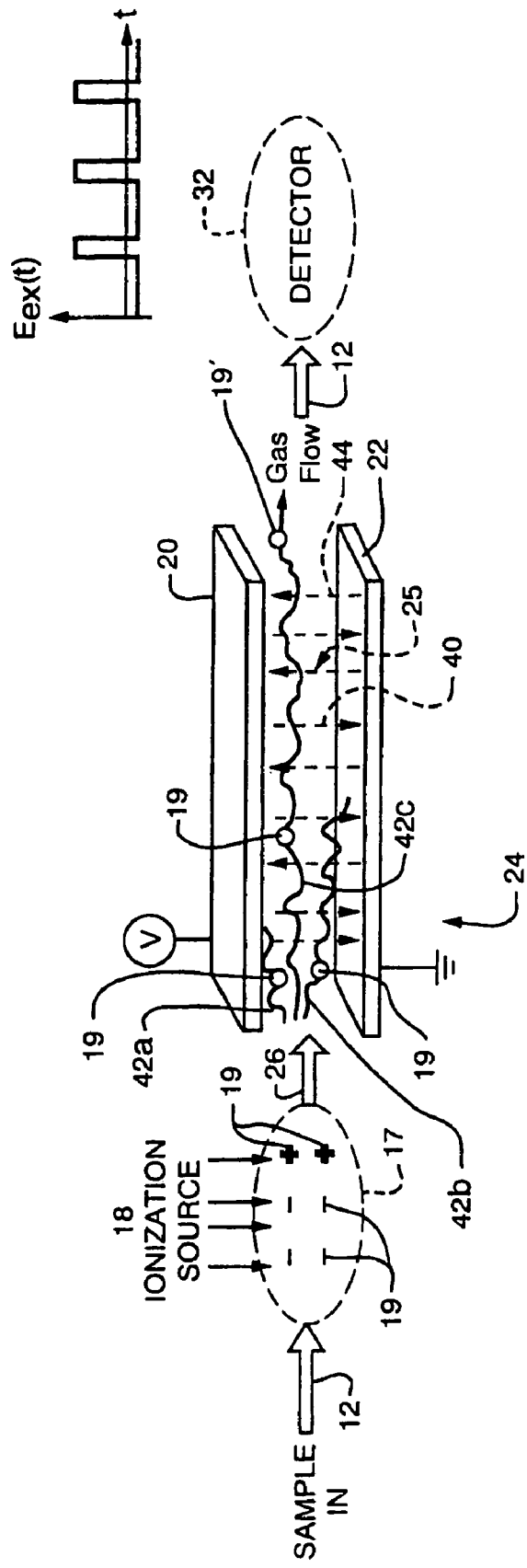
FIG. 2 is a schematic representation of the ions as they pass through the filter electrodes of FIG. 1 toward the detector.

More specifically, as shown in FIG. 2, ions 19 flow in the alternating asymmetric electric field 25, in oscillating paths 42a, 42b and 42c. The time varying RF asymmetric voltage V applied to the filter electrodes is typically in the range of ±(1000-10,000) volts and creates electric field 25 with a maximum field strength of around 40,000 V/cm. The path taken by a particular ion is mostly a function of its size, cross-section and charge. Where the asymmetric field is not compensated for the resulting high-low-field offset imposed on the ions, then the ions will reach and contact electrode 20 or 22 and will be neutralized. Thus as compensation is applied to the filter field, a particular ion species will be returned back toward the center of the flow path and will pass through the filter for detection.

In a particular embodiment, compensation is achieved by applying a compensation field 44, typically in the range of ±2000 V/cm from an applied ±100 volt dc voltage, for example, applied concurrently and induced at, adjacent to, or between, electrodes 20 and 22, via a bias voltage applied thereto. Now a selected ion species 19' passes through filter 24 for detection.

In one embodiment, compensation field 44 is a constant bias which offsets alternating asymmetric field 25 to allow the selected ion species 19' to pass to detector 32. Thus, with the proper bias voltage, a particular species of ion will follow path 42c while undesirable ions will follow paths 42a and 42b to be neutralized as they encounter electrode plates 20 and 22.

Figure 3A:
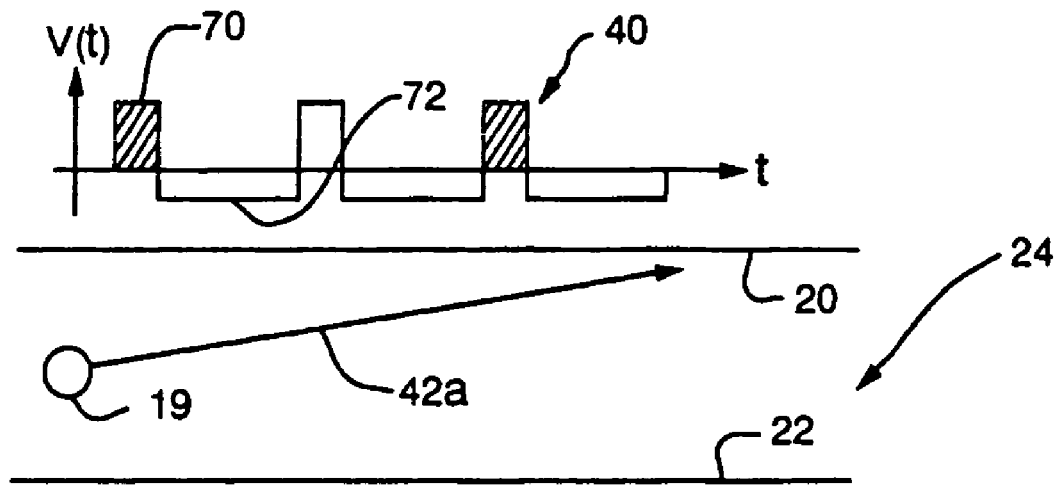
FIGS. 3A, 3B provide graphical representation of an asymmetric periodic voltage having a compensating varying duty cycle, for filtering unwanted ions (FIG. 3A) and passing through the filter selected ion species (FIG. 3B) without a bias voltage.
Figure 3B:
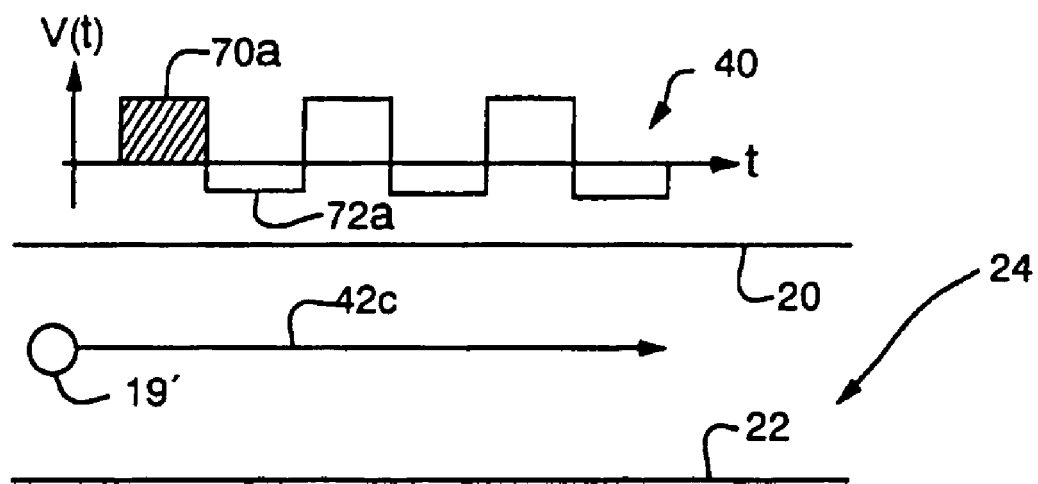

In an alternative practice of the invention, the duty cycle of the asymmetric periodic voltage applied to electrodes 20 and 22 of filter 24 is varied so that there is no need to apply a compensation voltage. The control electronics varies the duty cycle of asymmetric alternating electric field 25, with the result that path of a selected ion species (defined mostly by charge and cross-section, among other characteristics, of the ions) is returned toward the center of the flow path, and so to pass on for detection. As an example, and not by way of limitation, the duty cycle of field 25 may be one quarter: 25% high, peak 70, and 75% low, valley 72; in which case, ions 19 on path 42a approach and collide with a filter electrode 20 and are neutralized (FIG. 3A). However, by varying the duty cycle to 40%, peak 70a, 60% low, valley 72a, ions 19' on path 42c pass through filter 24 and toward the detector without being neutralized. Typically the duty cycle is variable from 10-50% high and 90-50% low (FIG. 3B). Accordingly, by varying the duty cycle of field 25 an ion's path in field 25 may be corrected so that it will pass through filter 24 without being neutralized and without the need for a compensating bias voltage.

Ions 19' that pass through filter 24 are now delivered for detection, which may be on-board or not. In a preferred embodiment, the detector is on board and is in the flow path. In one embodiment, detector 32 includes a biased top electrode 33 at a voltage and a biased bottom electrode 35, possibly at ground, formed on the same substrates as the filter electrodes. Top electrode 33 can be set at the same polarity as the ions to be detected and therefore deflects ions toward electrode 35. However, either electrode may detect ions depending on the passed ion species and bias applied to the electrodes. Moreover, multiple ions may be detected by using top electrode 33 as one detector and bottom electrode 35 as a second detector.

The output of FAIMS spectrometer 10 is a measure of the amount of charge detected at detector 32 for a given RF field 25 and compensation. The longer the filter 24 is set at a given compensation level, the more of a given species will be passed and the more charge will accumulate on detector 32.

Alternatively, by sweeping compensation over a predetermined voltage range, a complete spectrum for the sample and gas can be achieved. A FAIMS spectrometer according to the present invention requires typically less than thirty seconds and as little as one second or less to produce a complete spectrum for a given gas sample. Thus, by varying compensation during a scan, a complete spectrum of the gas sample can be generated.

Figure 4:
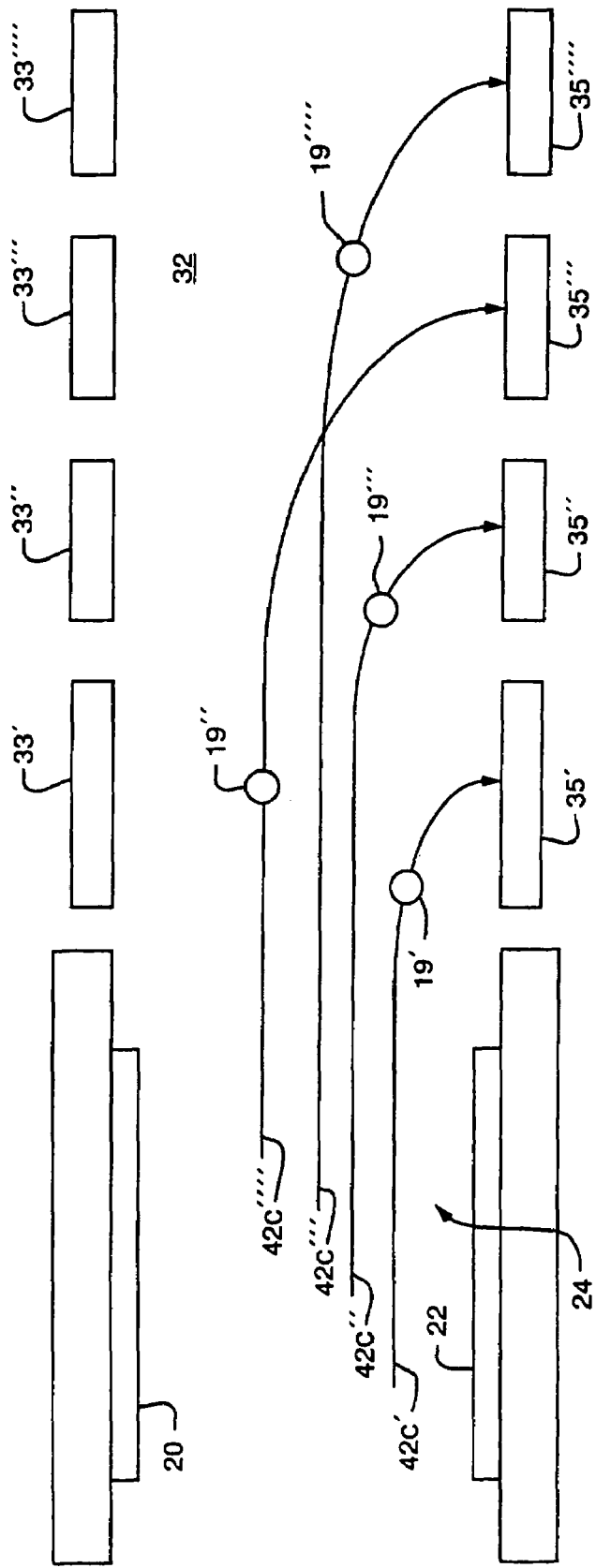
FIG. 4 is a schematic diagram of a segmented detector embodiment of the invention.

To improve FAIMS spectrometry resolution even further, detector 32, may be segmented, as shown in FIG. 4. As ions pass through filter 24 between filter electrodes 20 and 22, the individual ions 19'-19"" may be detected spatially, the ions having their trajectories 42c'-42c"" determined according to their size, charge and cross section. Thus detector segment 33' will have a concentration of one species of ion while detector segment 33" will have a different ion species concentration, increasing the spectrum resolution as each segment may detect a particular ion species.

Figure 5A:
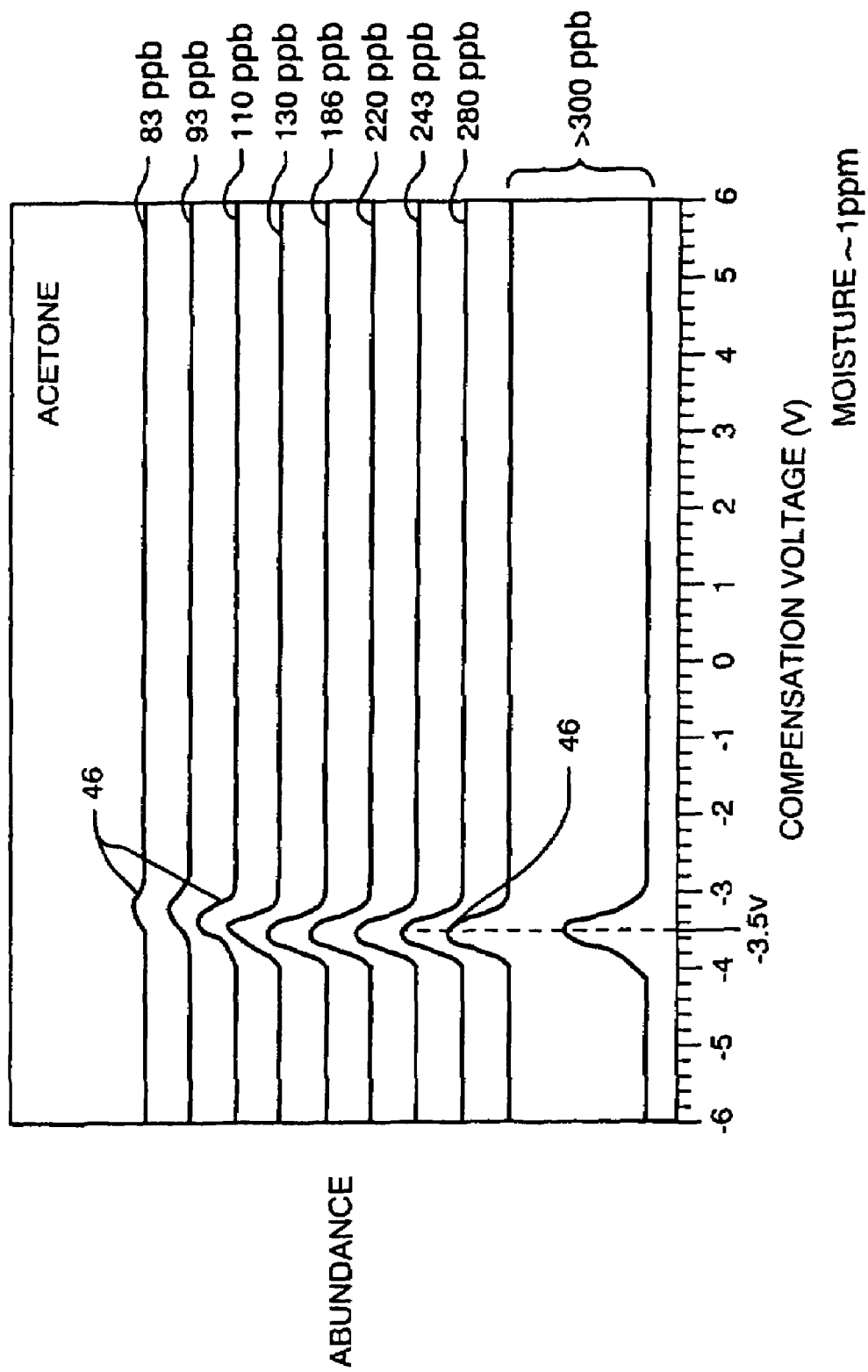
FIGS. 5A, 5B are graphical representations of the spectrometer response to varying concentrations of acetone and di-ethylmethyl amine in an embodiment of the invention.
Figure 5B:
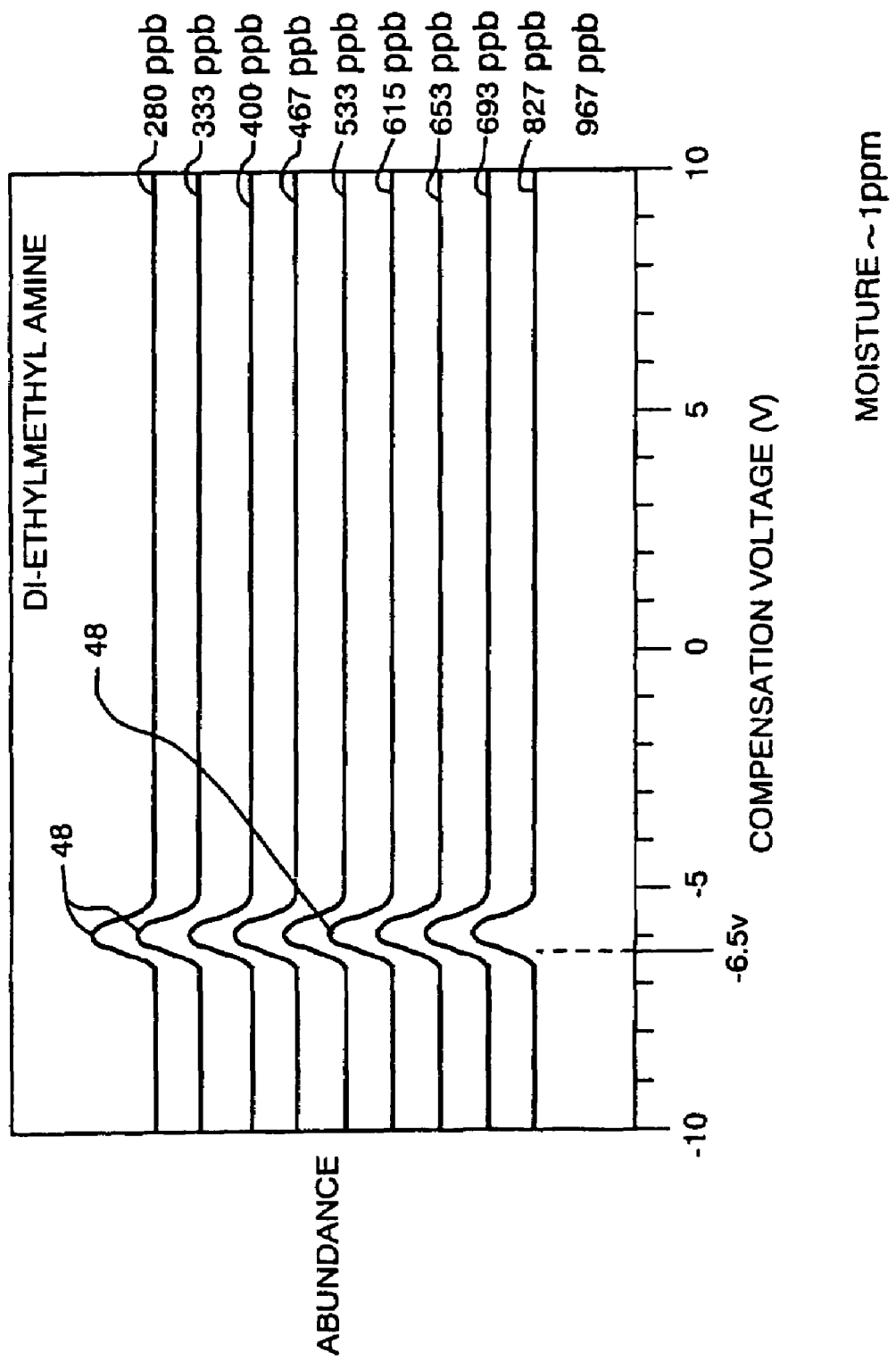

A PFAIMS spectrometer as set forth herein is able to detect and discriminate between a wide range of compounds, and can do so with high resolution and sensitivity. As shown in FIG. 5A, varying concentrations of acetone that were clearly detected in one practice of the invention, with definitive data peaks 46 at −3.5 volts compensation. These were detected even at low concentrations of 83 parts per billion. With the bias voltage set at −6.5 volts, FIG. 5B, varying concentrations of diethyl methyl amine were clearly detected in practice of the invention, generating data peaks 46; these were detected in concentrations as low as 280 parts per billion.

Figure 6:
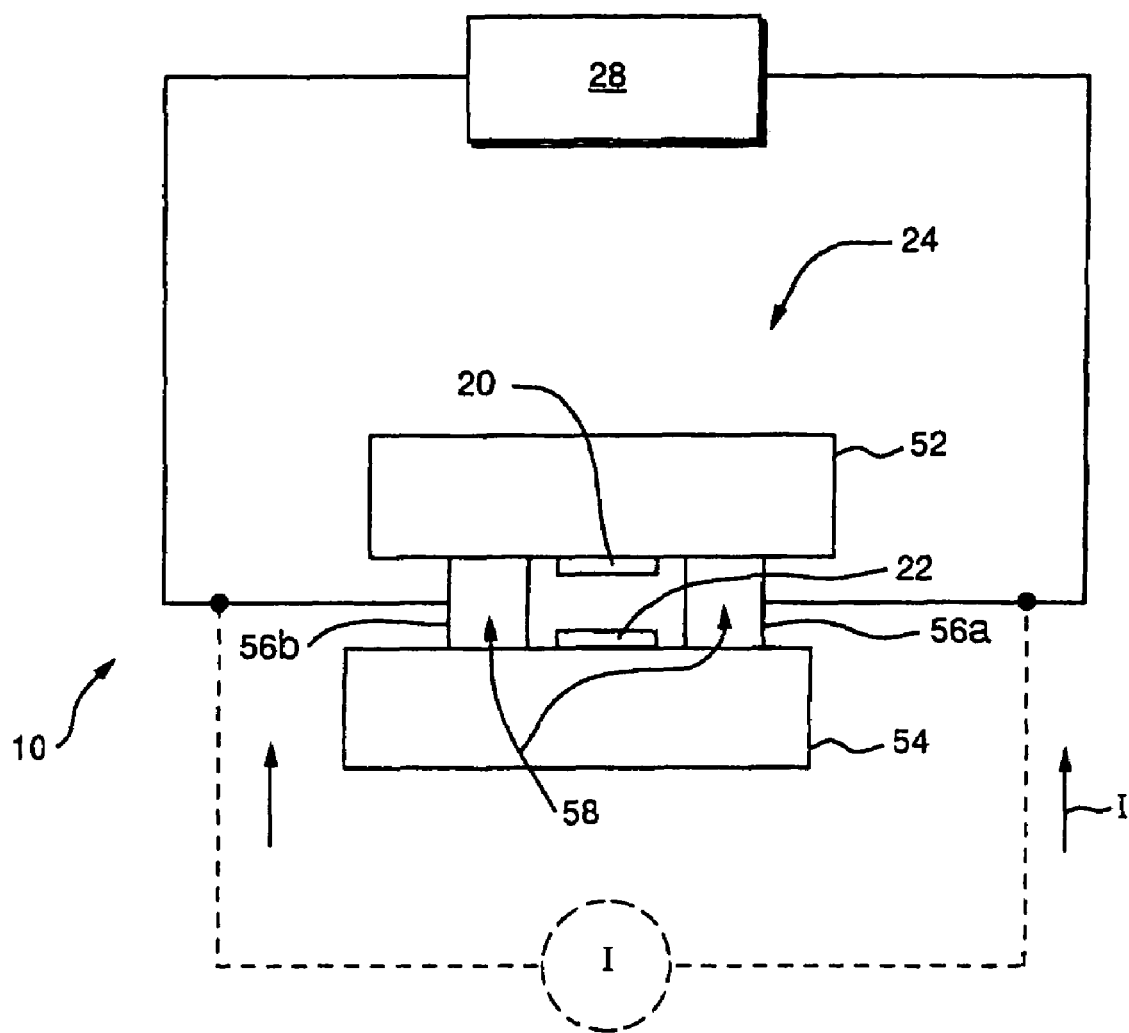
FIG. 6 is a cross sectional view of a spaced, micromachined filter assembly according to an embodiment of the present invention.
Figure 7:
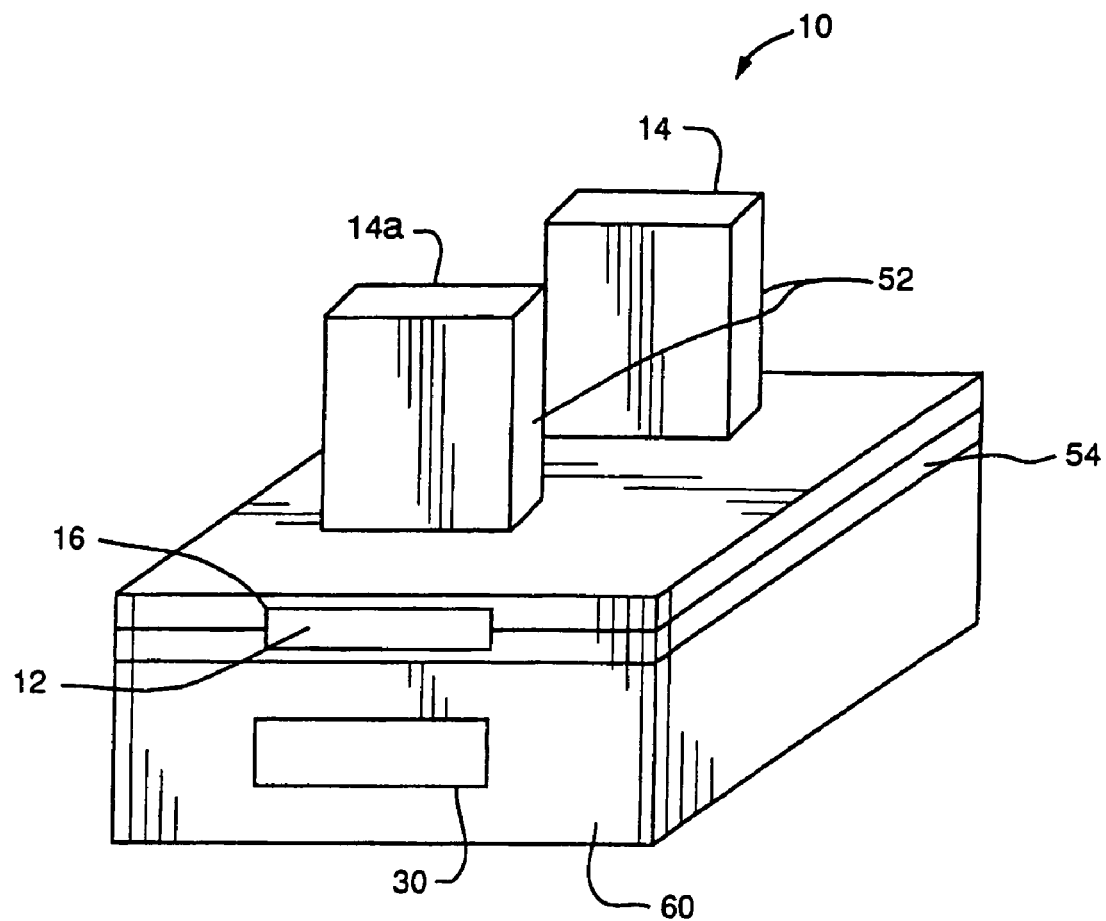
FIG. 7 is a perspective view of a practice of the invention as a packaged micromachined filter and detection system, including pumps, in miniaturized format.

Turning to FIG. 6 and FIG. 7, an embodiment of spectrometer 10 includes spaced substrates 52 and 54, for example glass or ceramic, and electrodes 20 and 22, which may be for example gold, titanium, or platinum, mounted or formed on substrates 52 and 54, respectively. Substrates 52 and 54 are separated by spacers 56a-b which may be formed by etching or dicing silicon wafer. The thickness of spacers 56a, 56b defines the distance between electrodes 20 and 22.

In one embodiment, a voltage is applied to silicon spacers 56a-b, ±(10-1000 volts dc), which transforms spacers 56a and 56b into electrodes to produce a confining electric field 58. Field 58 guides or confines the ions' paths to the center of flow path 26 in order to obtain more complete sample collection. As will be understood by a person skilled in the art, spacer electrodes 56a-b must be set to the appropriate voltage so as to "push" the ions toward the center of flow path 26. More ions traveling in the center of the path makes possible the result of more ions striking electrodes 33 and 35 for detection. However, this is not a necessary limitation of the invention.

Embodiments of the invention are compact with low parts count, where the substrates and spacers act to both contain the flow path and also to for a structural housing of the invention. Thus the substrates and spacers serve multiple functions, both for guiding the ions and for containing the flow path.

In order to further assure accurate and reliable operation of spectrometer 10, neutralized ions which accumulate on electrode plates 20 and 22 are purged. In one embodiment this may be accomplished by heating flow path 26. For example, controller 30, FIG. 1, may include current source 29, shown in phantom in FIG. 6, which provides, in response to microprocessor 36, a current I to electrode plates 20 and 22 to heat the electrodes for removing accumulated neutrals. Optionally, current I may additionally or instead be applied to spacer electrodes 56a and 56b, to heat flow path 26 to purge electrodes 20 and 22.

A packaged FAIMS spectrometer 10 may be reduced in size to perhaps one inch by one inch by one inch. Pump 14 is mounted on substrate 52 for drawing gas sample 12 into inlet 16. Clean dry air may be introduced into flow path 26 by recirculation pump 14a prior to or after ionization of the gas sample. Electronic controller 30 may be etched into silicon control layer 60 which combines with substrates 52 and 54 to form a housing for spectrometer 10. Substrates 52 and 54 and control layer 60 may be bonded together, for example, using anodic bonding, to provide an extremely small FAIMS spectrometer. Micro pumps 14 and 14a provide a high volume throughput which further expedites the analysis of gas sample 12. Pumps 14 and 14a may be, for example, conventional miniature disk drive motors fitted with small centrifugal air compressor rotors or micromachined pumps, which produce flow rates of 1 to 4 liters per minute.

In practice of ion detection, generally speaking, sample ions tend to be found in either monomer or cluster states. It has been found that the relationship between the amount of monomer and cluster ions for a given ion species is dependent of the concentration of sample and the particular experimental conditions (e.g., moisture, temperature, flow rate, intensity of RF-electric field). Both the monomer and cluster states provide useful information for chemical identification. It will be useful to investigate the same sample separately in a condition which promotes clustering and in an environment that promotes the formation of only the monomer ions. A two channel PFAIMS of an embodiment such as shown in FIG. 8 can be used toward this end.

Figure 8:
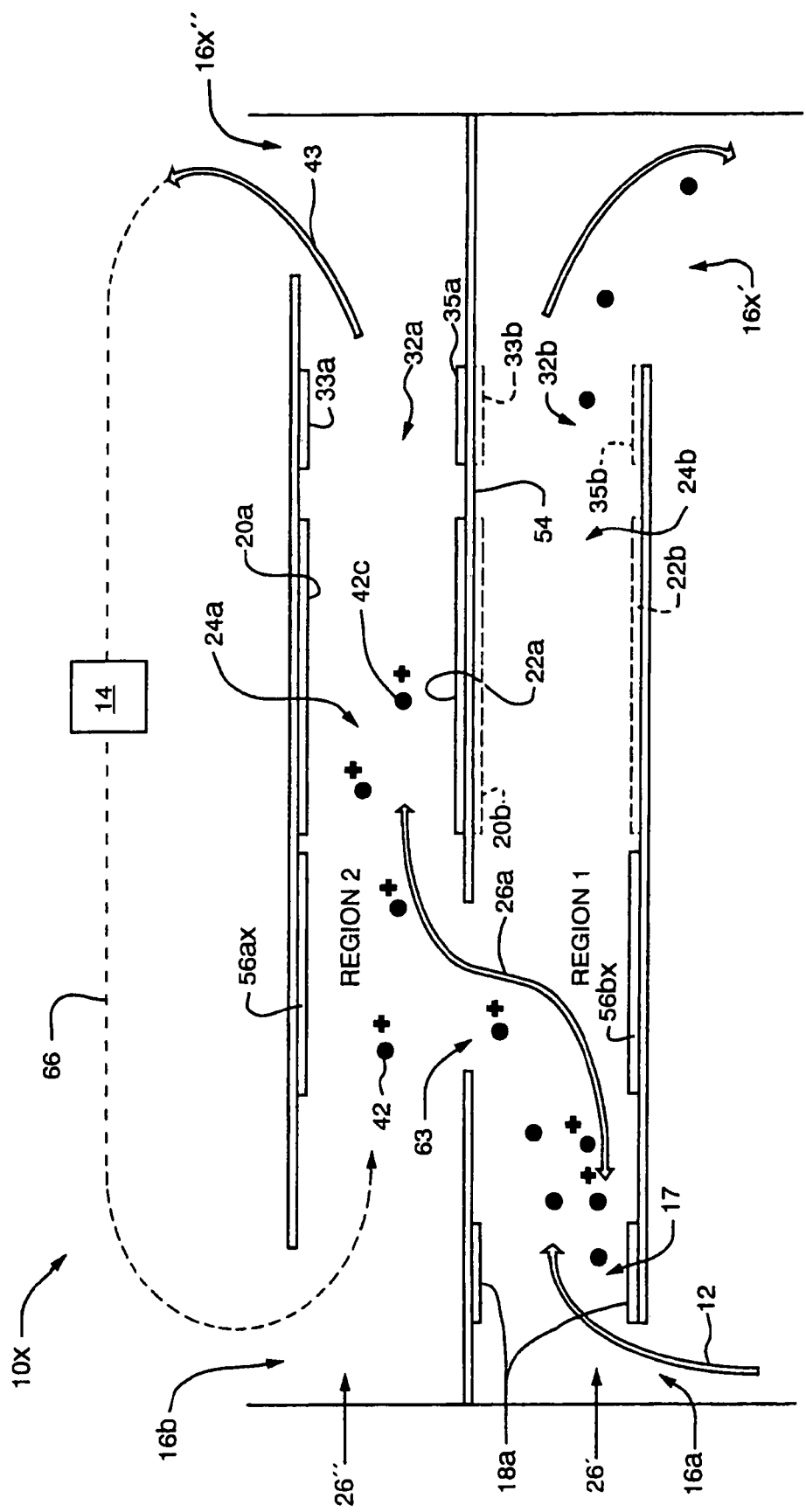
FIG. 8 is a cross sectional view of a dual channel embodiment of the invention.

Dual chamber embodiment 10x of the invention, FIG. 8, has two enclosed flow paths 26', 26" coupled by passageway 63. The gas sample 12 enters inlet 16a and is ionized at ionization region 17 in the lower flow path 26', ionized by any ionization device, such as an internal plasma source 18a. The ions are guided toward ion filter 24a in upper flow path 26" through passageway 63 by electrodes 56ax and 56bx, which act as steering or deflecting electrodes, and may be defined by confining electrodes 56a, 56b. As these ions 42c pass between ion filter electrodes 20a and 22a, undesirable ions will be neutralized by hitting the filter electrodes while selected ions will pass through filter 24a to be detected by detector 32a, according to the applied RF and compensation. By deflecting ions out of the gas flow, a preliminary filtration is effected, wherein the non-deflected ions and non-ionized sample and associated carrier gas will be exhausted at outlet 16x'. The exhaust gas 43 from upper flow path 26", at outlet 16x", may be cleaned, filtered and pumped via pump part 14a and returned at inlet 16b as clean filtered gas 66 back into the flow path 26".

In one practice of the invention, clean dry air 66a may be introduced into flow path 26 through clean air inlet 66 via pump 14. Drawing in clean dry air assists in reducing the FAIMS spectrometer's sensitivity to humidity. Moreover, if the spectrometer is operated alternately with and without clean dry air, and with a known gas sample introduced into the device, then the device can be used as a humidity sensor since the resulting spectrum will change with moisture concentration from the standardized spectrum for the given known sample.

In operation of the embodiment of FIG. 8, independent control of the flow rates in flow paths 26', 26" may be made. This means that a higher or lower flow rate in flow path 26' of the sample can be used, depending on the particular front end environment system, while the flow rate of the ions through the ion filter in flow path 26" can be maintained constant, allowing, consistent, reproducible results.

In practice of this embodiment, the upper ion filter region in flow path 26" can be kept free of neutrals. This is important when measuring samples at high concentrations, such as those eluting from a GC column. Because the amount of ions the ionization source can provide is fixed, if there are too many sample molecules, some of the neutral sample molecules may cluster with the sample ions and create large molecules which do not look at all like the individual sample molecules. By injecting the ions into the clean gas flow in flow path 26", and due to the effect of the high voltage high frequency field, the molecules will de-cluster, and the ions will produce the expected spectra.

Another advantage of the embodiment of FIG. 8 is that the dynamic range of the PFAIMS detector can be extended when employing a front end device (such as a GC, LC or electrospray for example). In one practice of the invention, by adjusting the ratios of the drift gas and GC-sample/carrier gas volume flow rates coming into ionization region 17, the concentration of the compounds eluting from the GC can be controlled/diluted in a known manner so that samples are delivered to the PFAIMS ion filter 24 at concentrations which are optimized for the PFAIMS filter and detector to handle. In addition, steering electrodes 56ax, 56bx can be pulsed or otherwise controlled to determine how many ions at a given time enter into flow path 26".

In a further practice of the embodiment of FIG. 8, an additional PFAIMS filter 24b may be provided in lower flow path 26' for detection of ion species that have not been deflected into flow path 26" and thus that pass into filter 24b. Filter 24b includes electrodes 20b, 22b, shown in phantom, and possibly also detector 32b having electrodes 33b, 35b, in phantom.

In the embodiment of FIG. 8, different gas conditions may be presented in each flow path. With a suitable control applied to the two steering electrodes 56ax, 56bx, selection can be made as to which region the ions are sent. Because each chamber can have its own gas and bias condition, multiple sets of data can be generated for a single sample simultaneously. This enables improved species discrimination in a simple structure, regardless of whether or not a front end device (such as a GC) is used for sample introduction.

Figure 9:
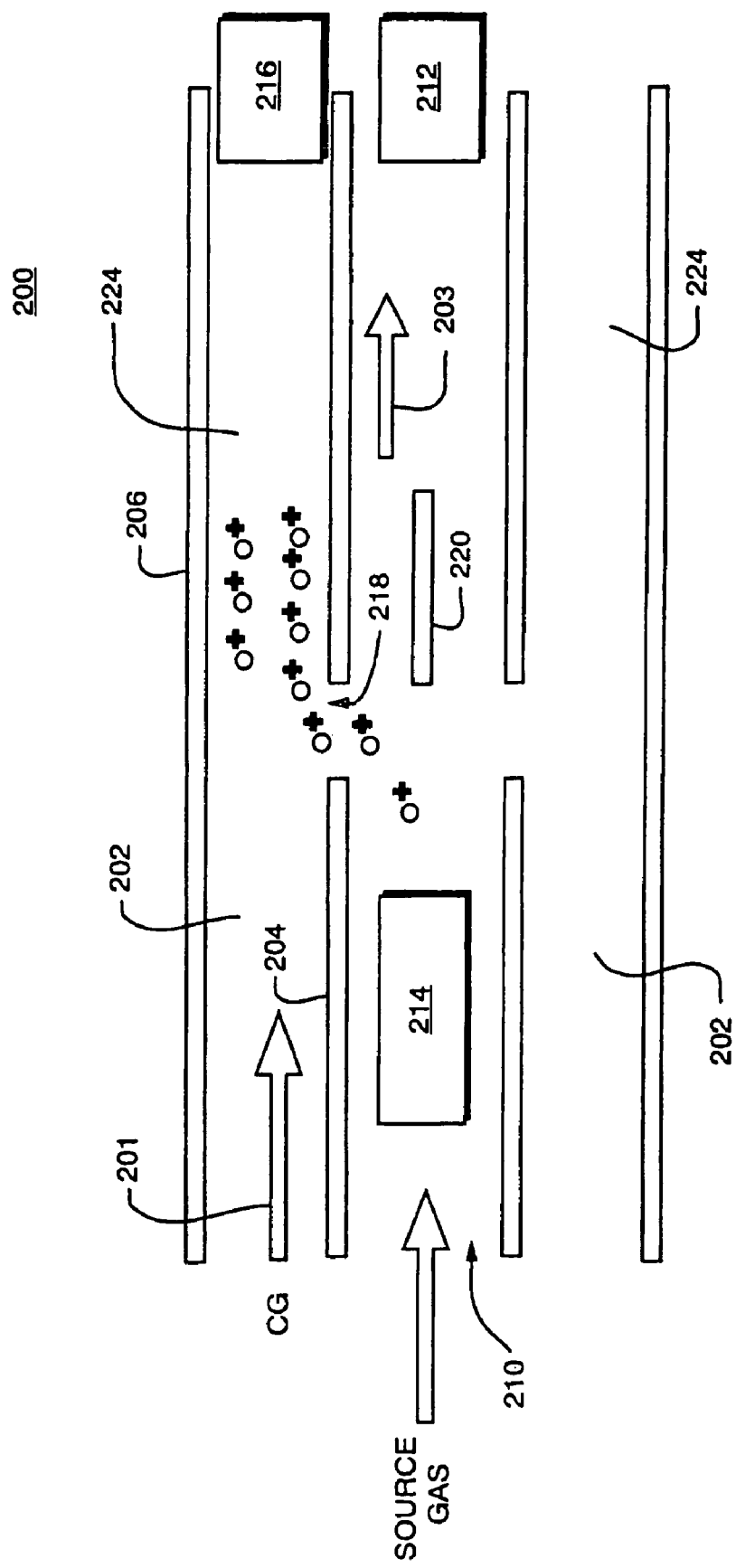
FIG. 9 is a schematic view of a prior art spectrometer.

One prior art ion mobility spectrometer 200, FIG. 9, (See U.S. Pat. No. 5,420,424), includes analytical gap 202 defined by the space between inner cylindrical filter electrode 204 and outer cylindrical filter electrode 206 electrodes. A source gas having compounds to be analyzed is drawn through inlet 210 via the action of pump 212; the sample is ionized by ionization source 214. A carrier gas CG is introduced via pump 216 into analytical gap 202. Ions generated by ionization source 214 travel through aperture 218 by the action of electrode 220 and into analytical gap 202 and travel toward detector 224. Such a structure requires two pumps 212 and 216, and separate flow paths 201 and 203 for the source gas and the carrier gas. Thus, prior art mobility spectrometer 200 cannot be made very small, and requires sufficient power to operate the pumps 212 and 216.

Embodiments of the present invention overcome limitations of the prior art by providing field-driven ion transportations via an ion flow generator, where ions flow through an ion filter as carried by the ion transport field. The ion flow generator of the present invention relieves the gas flow requirements of the prior art. Various options are possible, including providing a low volume flow, no gas flow, or reverse gas flow, along the longitudinal axis of the flow path. The reverse flow can be a supply of clean filtered air in the negative z direction to keep the ion filter and detector regions free of neutrals and to help remove solvent, reduce clustering, and minimize the effects of humidity. The ion flow generator is preferably based on electric potentials, but may be practiced in magnetic embodiments, among others, and still remain within the spirit and scope of the present invention. Various embodiments follow by way of illustration and not by way of limitation.

Figure 10:
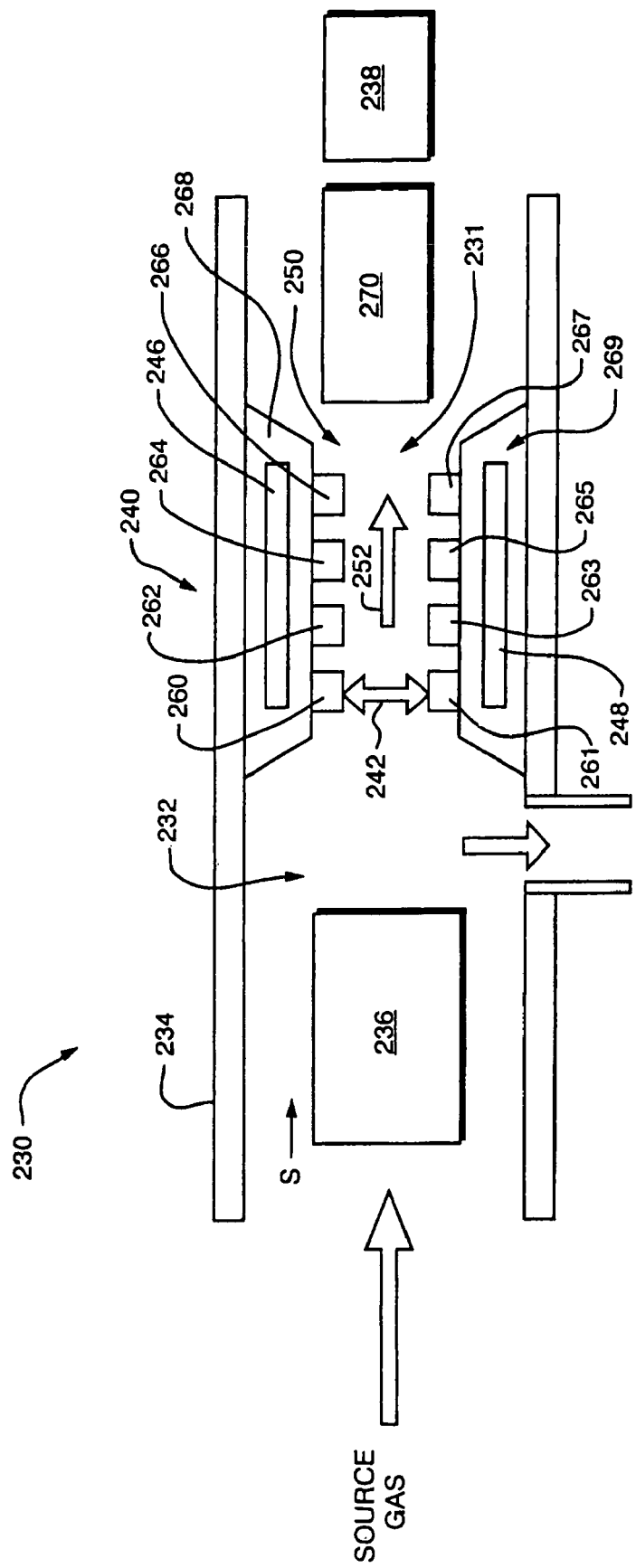
FIGS. 10-17 are respective schematic views of embodiments of the longitudinal field driven ion mobility spectrometer of the present invention.

In one practice of the invention, shown in FIG. 10, field asymmetric ion mobility spectrometer 230 includes a flow path 231 inside housing structure 234 (which may be formed by a round tube or a flat housing with walls defining an enclosure). A source gas carries sample S into the ionization region near the ionization source 236. This flow is supplied by pump 238, which may be a micromachined pump with a flow rate of much less than the typically required 1-4 liters per minute of the prior art (resulting in a power savings of between 1-5 watts over prior art spectrometers). Alternatively, this flow might be supplied by sample eluting from a GC column or the like.

Ion filter 240 is disposed in flow path 231 downstream from ionization source 236. Ion filter 240 creates the asymmetric electric field 242 (a compensated field 25), to filter ions generated by ionization of sample S. Ion filter 240 may include a pair of spaced electrodes 248 and 246 connected to an electric controller which applies a compensated asymmetric periodic voltage to electrodes 246 and 248.

In spectrometer 230, ion flow generator 250 provides longitudinal electric field transport for the ions. The strength of longitudinal electric field 252 can be constant or varying in time or space; the field propels ions through the filter asymmetric field 242, with ions passing through the filter according to their characteristics and the filter field compensation.

In the embodiment of FIG. 10, ion flow generator 250 includes discrete electrodes 260, 262, 264, and 266 supported by and insulated from filter electrode 246 by insulating medium 268, and discrete electrodes 261, 263, 265, and 267 supported by and insulated from filter electrode 248 by insulating medium 269. In one practice of the invention, electrodes 260, 261 are at 1,000 volts and electrodes 266, 267 are at 10 volts and electrode pairs 262, 263 and 264, 265 are at 500 and 100 volts, respectively, although these voltage levels vary or be varying depending on the specific implementation of spectrometer 230. There may be more or fewer electrodes opposing each other forming ion flow generator 250. Electrode pairs (260, 261), (262, 263), (264, 265), and (266, 267) can also each be a ring electrode as well as discrete planar electrodes. The strength of longitudinal electric field 252 propels ions generated at ionization source 236 through asymmetric electric field 242 and toward detector 270, thus eliminating or reducing the flow rate and power requirements of pumps 212 and 216, FIG. 9 of the prior art.

Typically, detector 270 (which may have the configuration shown earlier of two electrodes 33, 35 on substrates 52, 54) is positioned close to ion flow generator 250. Electrodes 260, 262, 264, 266, 261, 263, 265, and 267 preferably occupy more or less the same longitudinal space as ion filter 240 and its electrodes 246 and 248 relative to a gap 232 in flow path 231.

Figure 11:
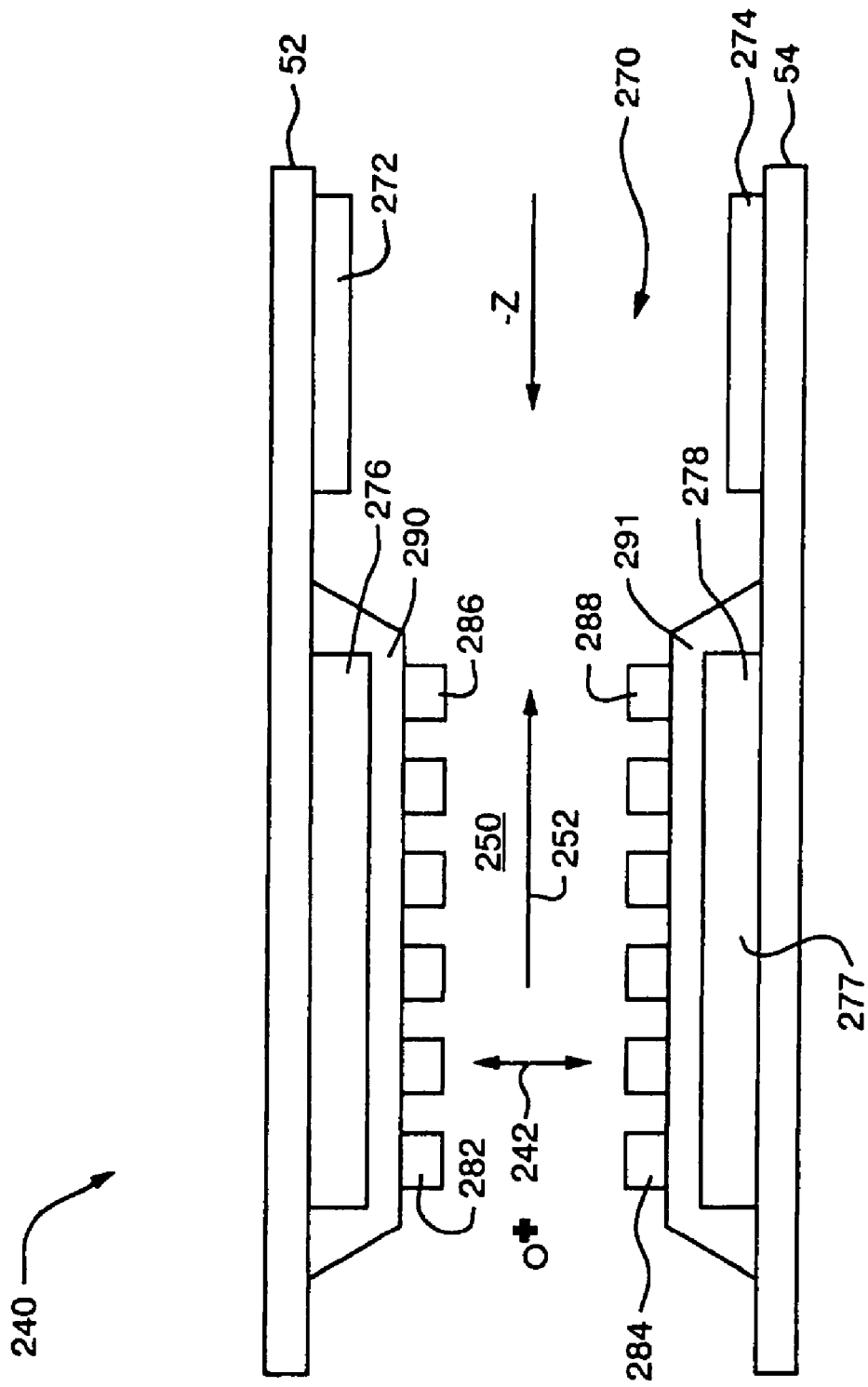

In the embodiment of the invention shown in FIG. 11, ion filter 240 includes spaced electrodes 276 and 277 for creating transverse filter field 242. The ion flow generator 250 includes spaced discrete electrodes, such as electrode pairs 282-284 and 286-288, for generating longitudinal transport field 252. In one practice, electrodes 282 and 284 are at 1000 volts and electrodes 286 and 288 are at 1000 volts. Insulating medium 290 and 291 insulates electrodes 282, 284, 286, and 288 with respect to electrodes 276 and 277. Electrode pair 282-284 could also be coupled as a single ring electrode and electrode pair 286-288 could be coupled also be a single ring electrode in a cylindrical embodiment of the invention.

It will be appreciated that the sample must be conveyed to the ionization region and the ions must be conveyed into the filter. In the design of FIG. 11, the ions are propelled by a low volume flow along the direction of the longitudinal electric field 252 to bring the ions proximate to electrodes 282-284. No gas flow is required in the ion filter and detector region due to longitudinal electric field 252. Also in this embodiment, a low flow volume of clean filtered air optionally can be provided in a direction opposite the longitudinal electric field to keep the ion filter and detector region free of neutrals. A resistive divider circuit or the like can be used to provide a potential gradient, so that for example, electrodes 282 and 284 are at 1000 volts while electrodes 286 and 288 are at 0 volts.

Figure 12:
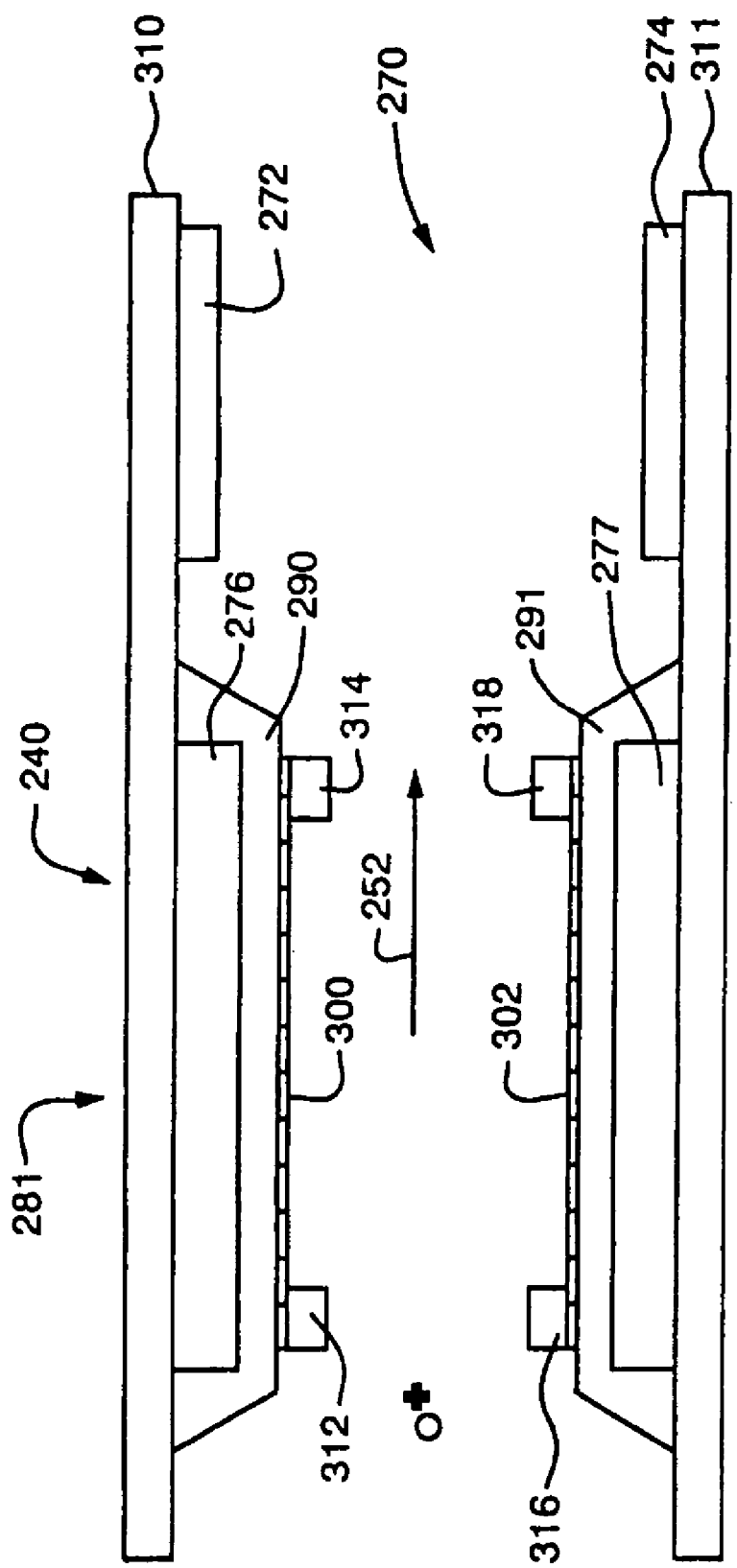

An alternative practice of the invention is shown in FIG. 12, having metal filter electrodes 276, 277 deposited on insulating substrates 310, 311 and filter electrodes 276, 277 coated with a thin insulator 290, 291. Metal electrodes, e.g., 312, 314, 316, 318, are formed under a resistive layer 300, 302, and the longitudinal field is generated between these electrodes. In one practice, ion filter 240 includes spaced resistive layers 300 and 302 insulated from electrodes 276 and 277 on insulating substrates 310, 311 by insulating medium 290 and 291, for example, a low temperature oxide material. Resistive layers 300 and 302 may be a resistive ceramic material deposited on insulating layers 290 and 291, respectively. Terminal electrodes 312, 314, 316 and 318 make contact with each resistive layer to enable a voltage drop across each resistive layer that generates the longitudinal electric field 252, for example, where electrodes 312 and 316 are at 1000 volts while electrodes 314 and 318 are at 0 volts. This embodiment can be extended to a cylindrical geometry by making electrodes 312 and 316 a ring electrode, electrodes 314 and 318 a ring electrode, and resistive layers 300 and 302 an open cylinder.

Figure 13:
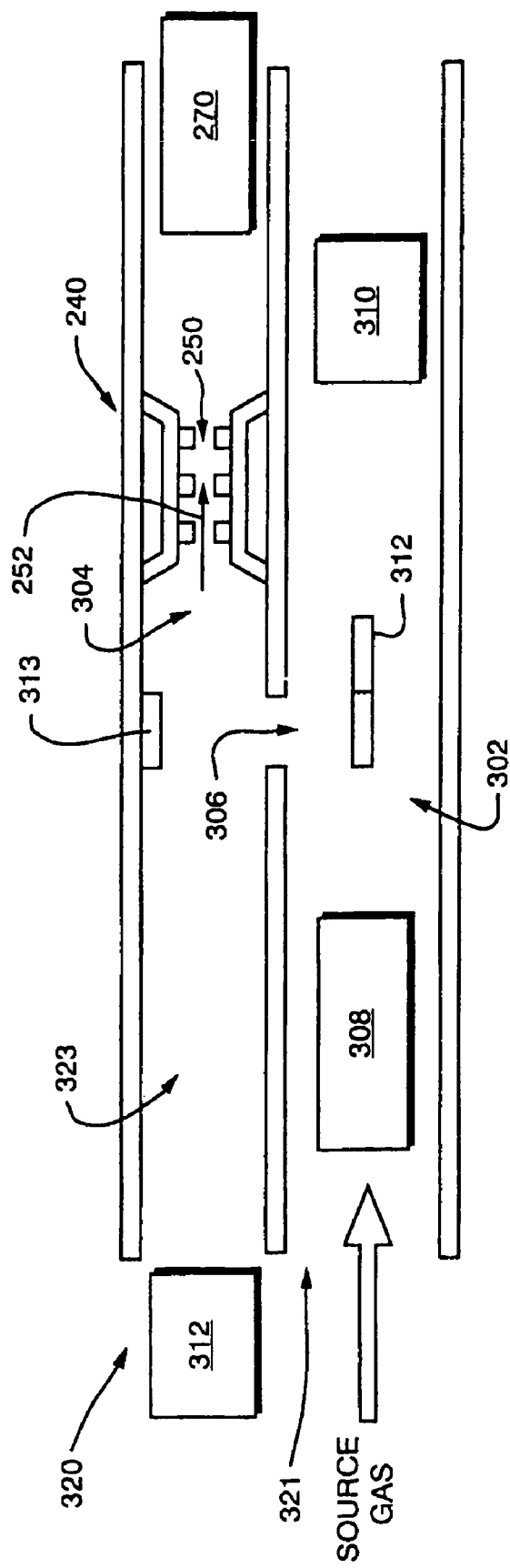

Continuing with the benefits of a dual flow path, such as earlier shown in FIG. 8, in the embodiment of FIG. 13 spectrometer 320 includes structure which also defines dual flow paths 321, 323. Ion filter 240 and ion flow generator 250 are defined by sets of electrodes in this embodiment. Gap 304 is defined in flow path 323 at filter 240. Opening 306 joins the flow paths. Source gas carrying sample S to be analyzed is drawn into flow path 302 by pump 310 and ionized by ionization source 308. The ions are deflected through opening 306 and into gap 304 assisted by deflecting electrodes 312 and 313. Ion flow generator 250 propels the ions through the asymmetric ion field at filter 240. Optionally pump 312 can be used to supply a low flow rate of air, possibly dehumidified, into, or recirculating through, gap 304, but no carrier gas flow is required in flow path 302. Ion species passed by the filter are carried by the ion transport 252 to detector 270.

Figure 14:
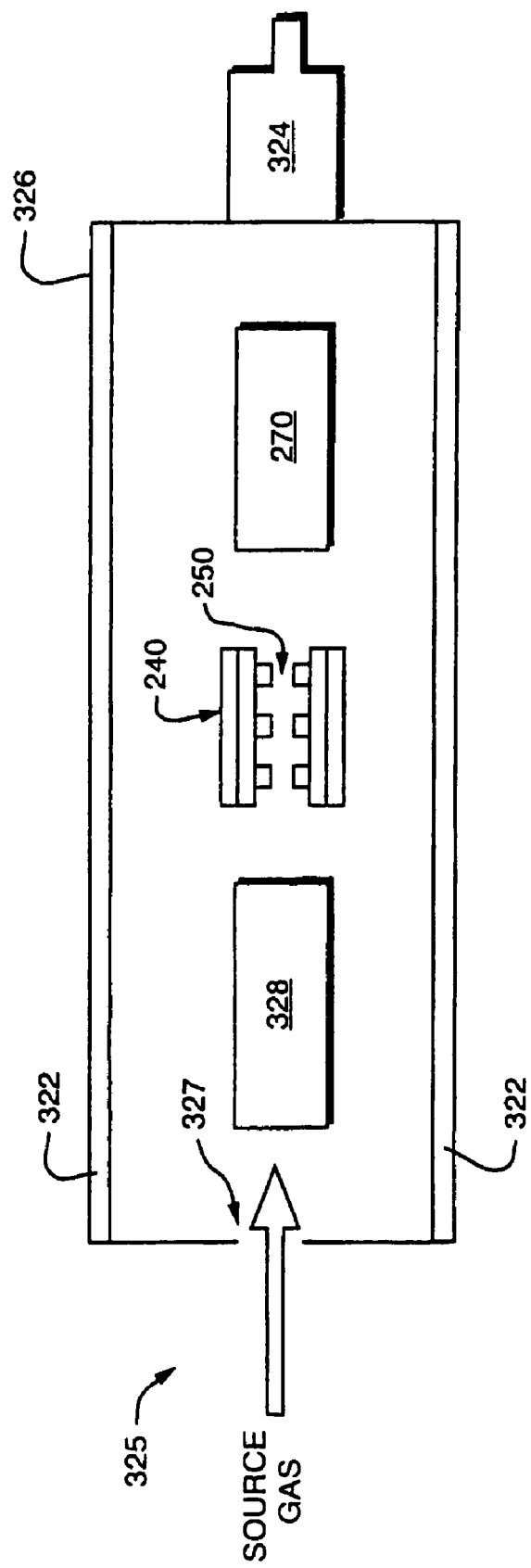

In another embodiment of the invention, shown in FIG. 14, spectrometer 325 includes a desiccant 322 chambered in housing 326 and small pump 324, which is the only pump required to draw source gas into housing 326 through a small orifice 327. Ionization source 328 produces ions which travel through filter 240 aided by the longitudinal electric field created by ion flow generator 250. The desiccant serves to further condition the sample gas before filtering for improved performance.

Figure 15:
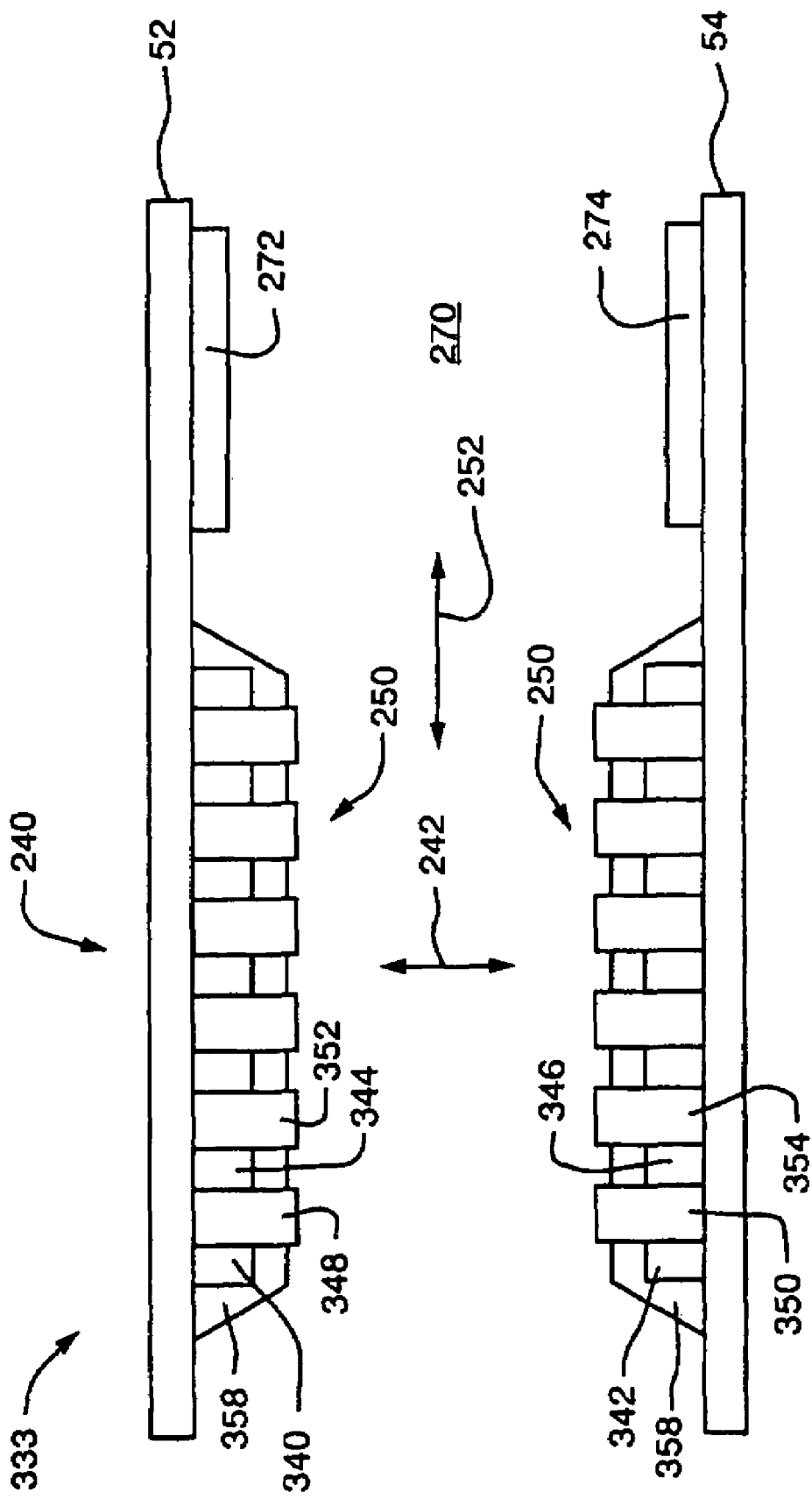

In still another embodiment shown in FIG. 15, spectrometer 333 includes ion filter 240 with a plurality of RF electrodes 340, 342, 344 and 346 connected to an electric controller 30 which applies the asymmetric periodic voltage to create the filtering field. DC compensation may also be applied to these electrodes. The ion flow generator 250 includes a second plurality of discrete electrodes 348, 350, 352 and 354 dispersed among but insulated from the discrete RF electrodes of the ion filter and connected to controller 30, which establishes a gradient between the electrodes to generate an ion propelling transport field 252 along the flow path toward the detector 270. The electrodes may be coated with an insulating material 358, as well as being isolated from each other by adequate insulation.

In the embodiment of FIG. 15, all the RF electrodes may be independently driven or tied together while the longitudinal field producing electrodes have a potential gradient dropped across them. In one embodiment, the voltages applied to the electrodes can be alternated so that first a voltage is applied to generate the transverse RF electric field 242 and then a voltage is applied to other or same electrodes to generate the longitudinal ion transport field 252.

Figure 16:
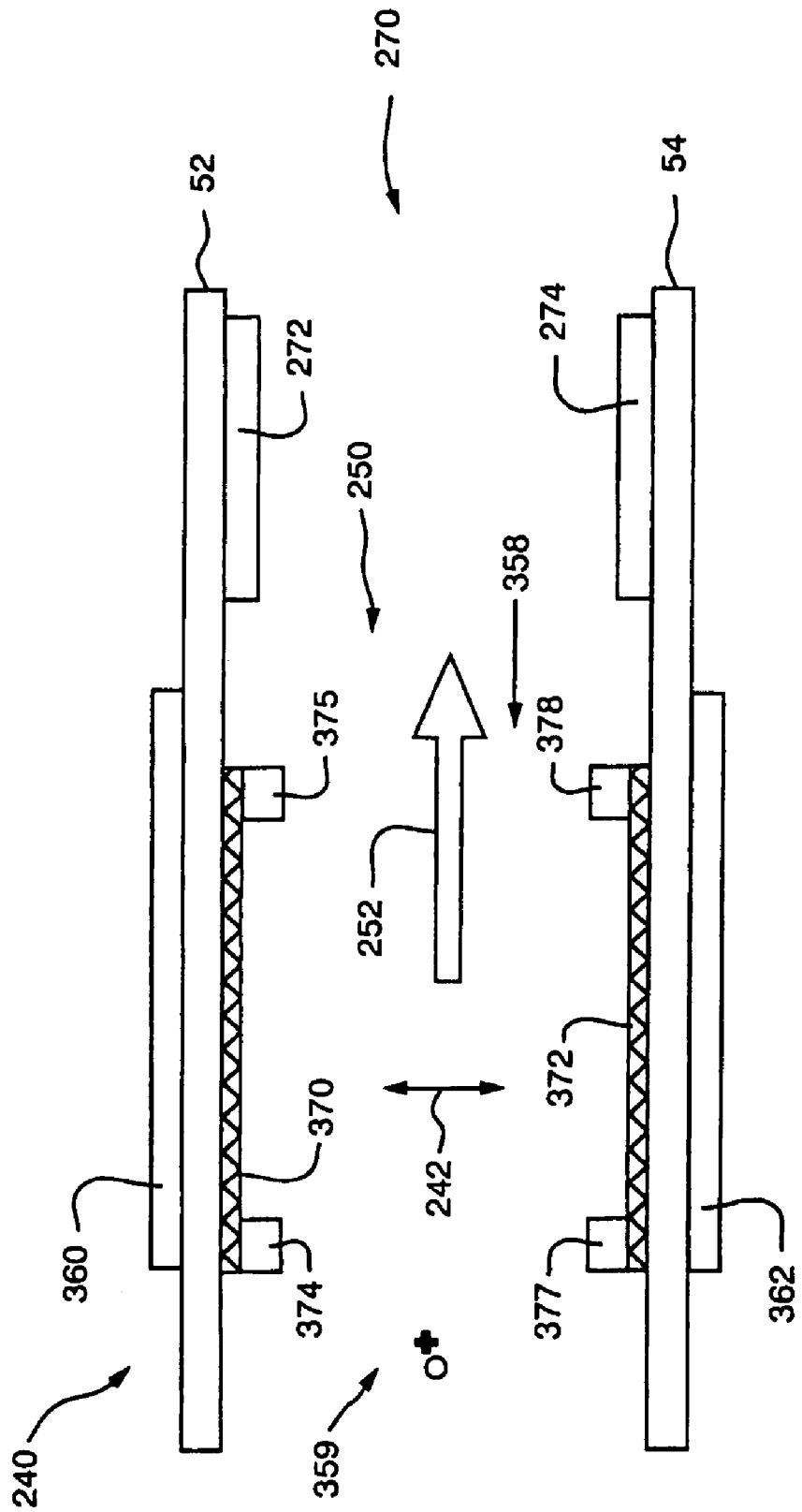

In still another embodiment, spectrometer embodiment 359 shown in FIG. 16 includes RF electrodes 360, 362, which provide the asymmetric ion filtering electric field 252 are disposed on the outside walls of insulative substrates 52, 54. Resistive layers 370 and 372 may be a resistive ceramic material deposited on the inside walls of insulating substrates 52 and 54, respectively. Terminal electrodes 374-375, and 377-378 make contact with each resistive layer is shown to enable a voltage drop across each resistive layer to generate the ion propelling longitudinal electric field 252. Thus, electrodes 374 and 377 may each be at −100 volts while electrodes 375 and 378 are at −1000 volts, for example.

Figure 17:
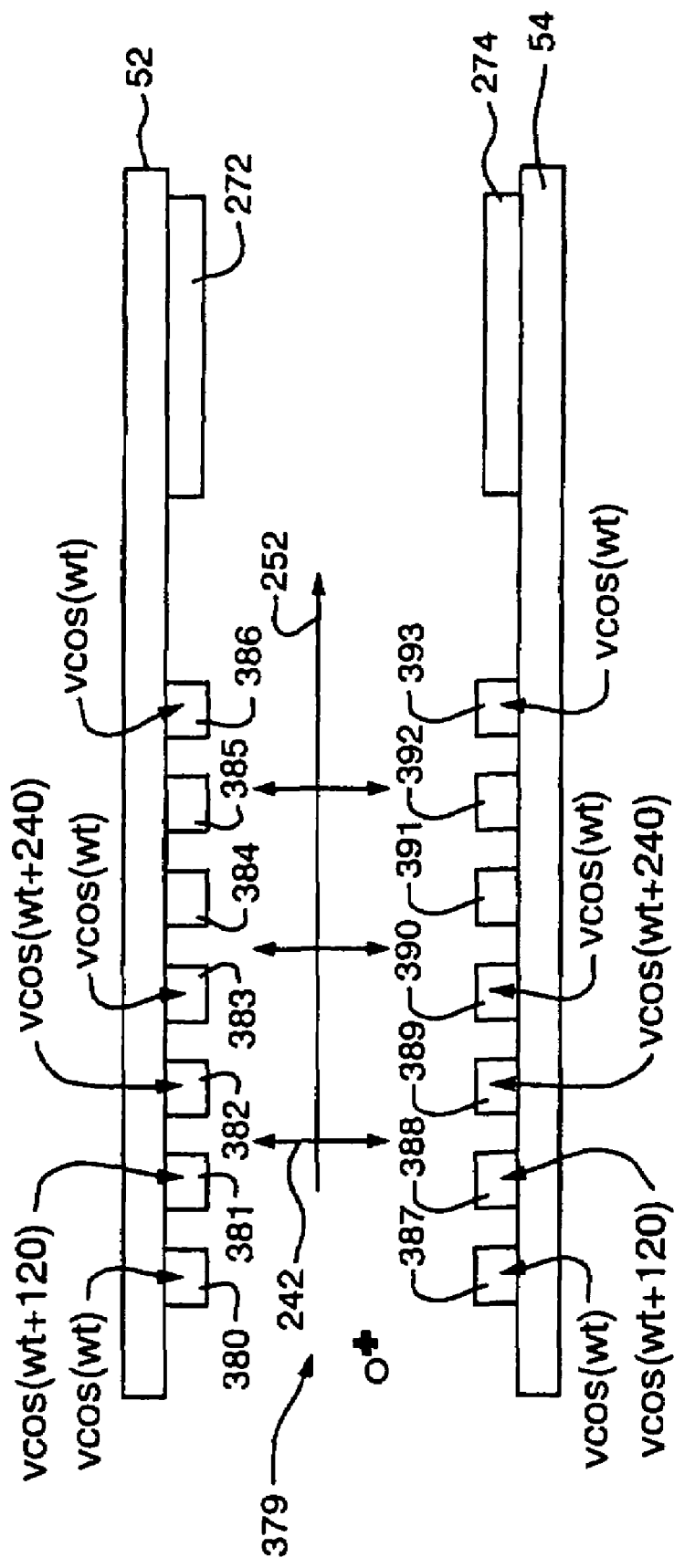

In the embodiment of FIG. 17, spectrometer 379 has discrete electrodes 380-386 on substrate 52 and 387-394 on substrate 54 which cooperate to produce an electrical field or fields. The net effect provides both transverse and longitudinal field components to both filter and propel the ions. A traveling wave voltage of the form $$V \cos(wt-kz)$$

where k=2 π/λ is the wave number has an associated electric field with both transverse and longitudinal components 242+ 252. For a planar system, each succeeding set of opposing electrodes is excited by a voltage source at a fixed phase difference from the voltage source applied to the adjacent set of opposing electrodes.

Thus, electrodes 380 and 387 are excited with a voltage of vcos(wt) while electrodes 381 and 388 are excited with a voltage of vcos (wt+120) and so on as shown in FIG. 17. Traveling wave voltages require multiphase voltage excitations, the simplest being a two phase excitation. So, a two conductor ribbon could also be wound around a duct defining the gap with one conductor excited at v cos(wt) and the other conductor excited at v sin(wt). Three phase excitations could be incorporated if the conductor ribbon or tape had three conductors.

In an alternative of the embodiment of FIG. 17, the discrete electrodes 380-386 and 387-394 are still driven to produce both transverse and longitudinal fields to both filter and propel the ions. The PFAIMS RF signal is applied to the electrodes to generate the transverse RF field, which may involve one electrode on each substrate or multiple electrodes. Compensation is also generated, either by varying the duty cycle or the like of the RF, or by applying a DC bias to the electrodes, which may involve one electrode on each substrate or multiple electrodes. Finally, the ion flow generator includes a selection of these electrodes biased to different voltage levels (e.g., 1000 vdc on electrodes 380 and 387 and 100 vdc on electrodes 386 and 393) to generate a gradient along the flow path. Compensation voltage applied to the RF filter field opens the filter to passage of a desired ion species if present in the sample as propelled by the flow generator. If the compensation voltage is scanned, then a complete spectrum of the compounds in a sample can be gathered.

Figure 18:
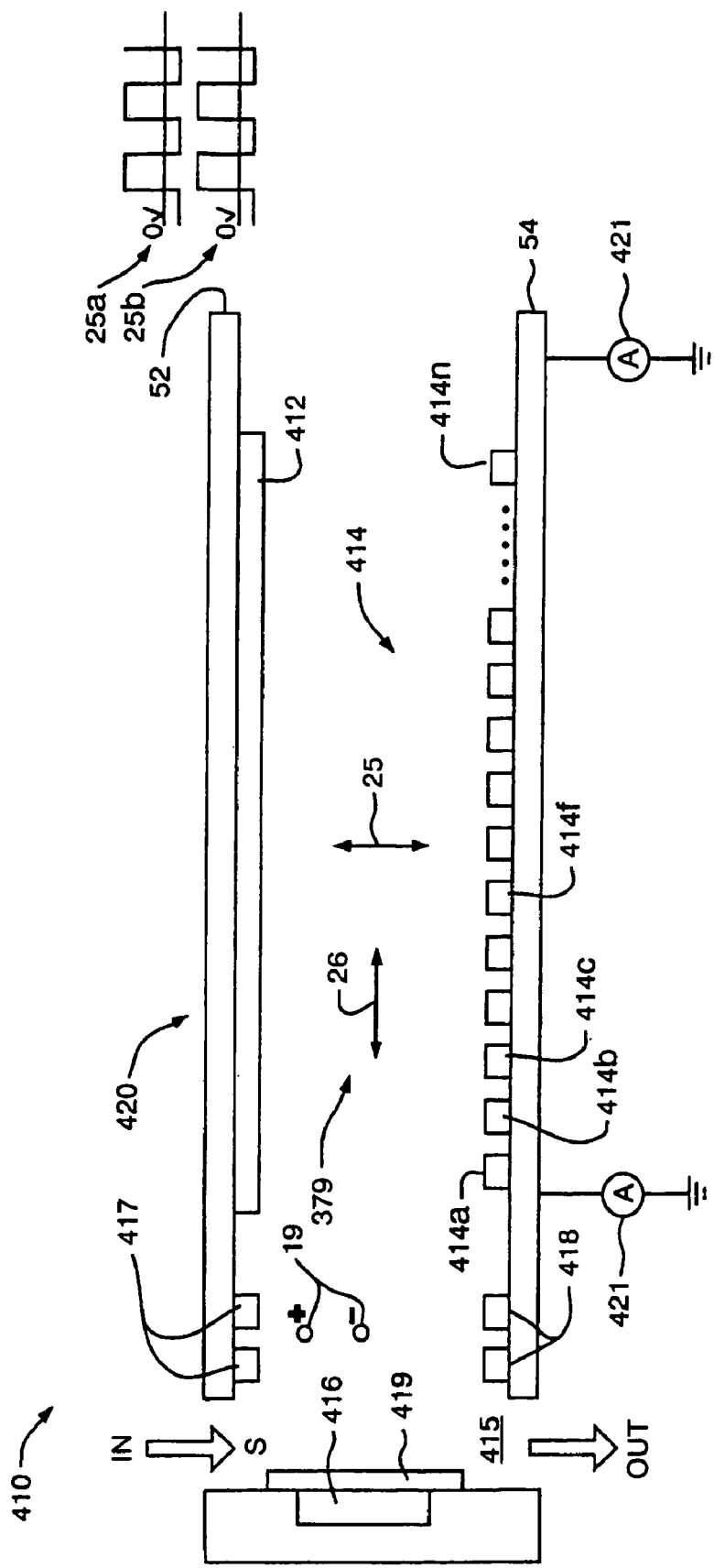
FIG. 18 is an embodiment of the invention that performs ion filtering based on ion trajectory within the filter region.

In a further embodiment of the invention, ion filtering is achieved without the need for compensation of the filter field. As shown in FIG. 18, in one illustrative embodiment, spectrometer 410 has a single RF (high frequency, high voltage) filter electrode 412 on substrate 52. A segmented filter-detector electrode set 414 on substrate 54 has a plurality of electrodes 414a-414n. Electrode 412 faces set 414 over flow path 26. Strips 414a-414n are maintained at virtual ground, while the asymmetric field signal is applied to the filter electrode 412.

It will be further appreciated that, referring to FIG. 2, ions 19 flow in the alternating asymmetric electric field 25 and travel in oscillating paths that are vectored toward collision with a filter electrode, and collision will occur in absence of adequate compensation. In the embodiment of FIG. 18, the absence of compensation favorably enables driving of the ions to various electrodes of the segmented electrode set 414. Thus all of the ions are allowed to reach and contact one of the electrodes 414a-414n. These ions thus deposit their charges upon such contact, which is monitored such as with current meters 421, 421. (It will be further appreciated that this arrangement is illustrative and not limiting. For example, the filter electrode may be segmented, similar to the filter-detector electrode set, where ions also will be detected thereon.)

In an illustrative embodiment, upstream biasing effects which ions flow to the filter. For example, a sample S flows ("IN") into an ionization region 415 subject to ionization source 416. Electrodes 417, 418, 419 are biased to deflect and effect flow of the resulting ions. Positive bias on electrode 419 repels positive ions toward the filter and electrodes 417, 418 being negatively biased attract the positive ions into the central flow of filter 420, while negative ions are neutralized on electrode 419 and which are then swept out ("OUT") of the region. Negative bias on electrode 419 repels negative ions toward the filter and electrodes 417, 418 being positively biased attract the negative ions into the central flow path 26 of filter 420, while positive ions are neutralized on electrode 419.

The path taken by a particular ion in the filter is mostly a function of ion size, cross-section and charge, which will determine which of the electrodes 414a-414n a particular species will drive into. This species identification also reflects the polarity of the ions and the high/low field mobility differences ("alpha") of those ions. Thus a particular ion species can be identified based on its trajectory (i.e., which electrode is hit) and knowledge of the signals applied, the fields generated, and the transport characteristics (such as whether gas or electric field).

In practice of the filter function, where the upstream biasing admits positive ions 19+ into the filter, those positive ions with an alpha less than zero will have a mobility decrease with an increase of the positively offset applied RF field (waveform 25a). This will effect the trajectory of these ions toward downstream detector electrode 414n. However, a positive ion 19+ with an alpha greater than zero will have a mobility increase with an increase of the negatively offset applied RF field (waveform 25b), which in turn will shorten the ion trajectory toward the nearer detector electrodes.

Similarly, where the filter is biased to admit negative ions, a negative ion 19– with an alpha less than zero will have a mobility increase with an increase of the positively offset applied RF field waveform 25a; this will tend to effect the ion trajectory toward downstream detector electrode 414n. However, a negative ion 19– with an alpha greater than zero will have a mobility increase with an increase of the negatively offset applied RF field waveform 25b, which in turn will tend to shorten the ion trajectory toward the nearer detector electrodes. Thus, ions can be both filtered and detected in spectrometer 410 without the need for compensation.

Figure 19:
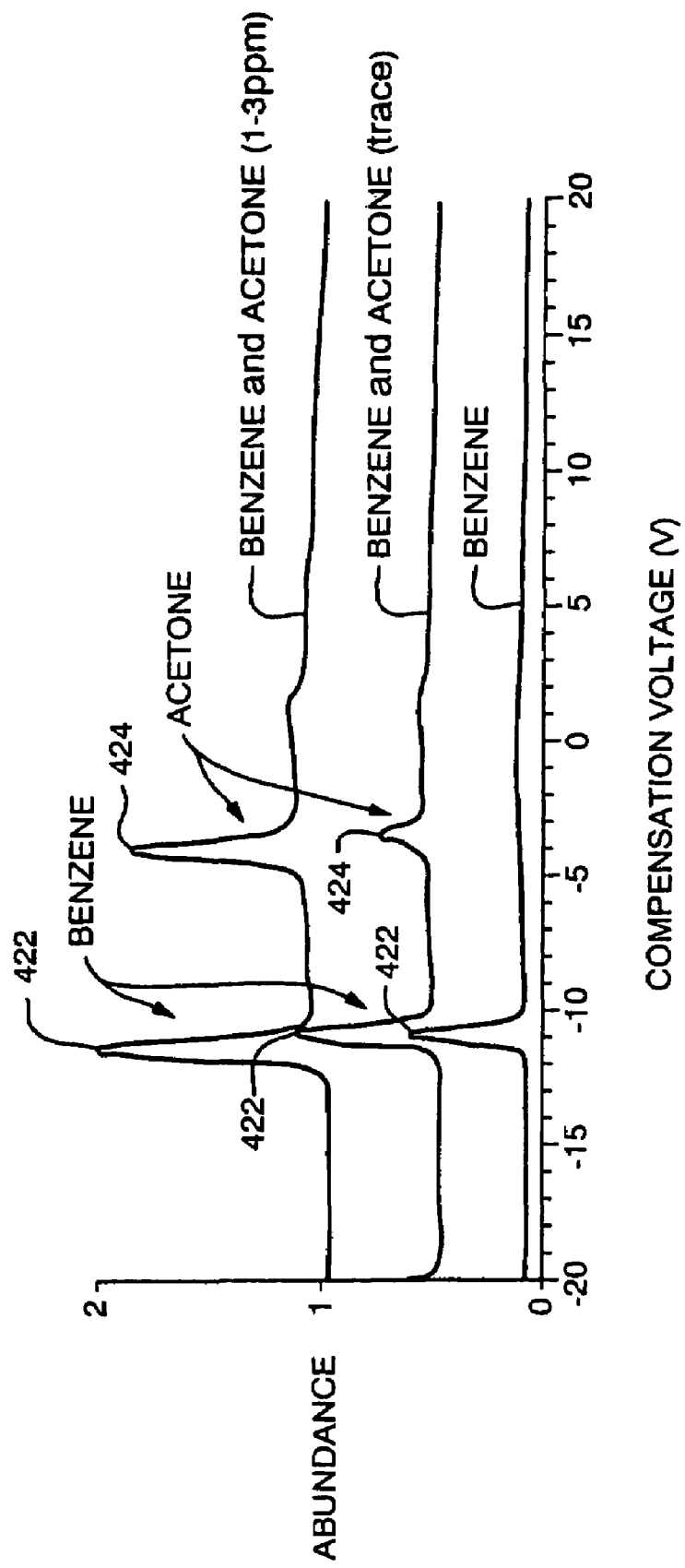
FIG. 19 is a graphical representation of identification of chemical constituents of a mixture (benzene and acetone) in practice of the invention.

Various embodiments of the present invention are able to identify compounds in a chemical sample down to trace amounts. In FIG. 19, identification of individual constituents of a mixture is demonstrated by the distinct and separate Benzene peaks 422 and acetone peaks 424 obtained in practice of the invention. Three plots are superimposed in FIG. 19. The first plot is for benzene and acetone (1-3) ppm; the second plot is for benzene and acetone (trace). The bottom plot shows benzene alone. It therefore can be observed that the acetone peak can be easily distinguished from the benzene peak in practice of the present invention. This capability enables separation and identification of a wide array of compounds in chemical samples in a compact and cost-effective method and apparatus of the invention.

Multiple use of electrodes is not limited to the examples set forth above. Embodiments of the present invention lend themselves to the use of an electrospray ionization source nozzle because certain of the electrodes can function both as the source for the PFAIMS and longitudinal electrical field which transports the ions toward the detector electrodes, but also as the electrospray electrodes which create a fine spray sample for ionization. Thus, in accordance with the present invention, pumps 216 and 212, FIG. 9 of the prior art are either eliminated or at least reduced in size and have lower flow rate and power requirements.

In practice of the invention, by the incorporation of an ion flow generator which creates a longitudinal electric field in the direction of the intended ion travel, the ions are propelled through the transversely directed compensated asymmetric electric field and onward for detection. The apparatus may include a detector or may deliver ions to a detector.

In practice of the invention, pump and gas flow requirements are simplified. By eliminating the high flow rate of pumps used in prior art spectrometers, a significant reduction in power consumption, size, and cost can be realized leading to a miniaturized spectrometer on a chip in practice of embodiments of the invention.

Another benefit in practice of alternative embodiments of the invention is that a flow of clean filtered air can be applied in a direction opposite the direction of the motion of the ions. In this way, any neutrals in the sample gas which were not ionized are deflected away and do not enter the ion analysis region. The result is the reduction or elimination of ion clustering, and reduction of the impact of humidity on sensor performance. Because the flow rates are low, it is possible to incorporate integrated micromachined components. Molecular sieves can be located close to the filter in order to absorb any neutral molecules in the analysis region to reduce or prevent clustering.

Embodiments of the present invention employ a field asymmetric ion mobility filtering technique that uses compensated high frequency high voltage waveforms and longitudinal e-field propulsion. The RF fields are applied perpendicular to ion transport, with a planar configuration, but coaxial, concentric, cylindrical and radial embodiments are also within the scope of the invention.

The spectrometer can be made extremely small, if required, and used in chemical and military applications, as a filter for a mass spectrometer, as a detector for a gas chromatograph, as a front end to a time of flight ion mobility spectrometer for increased resolution or as a filter for a flexural plate wave device.

The present invention provides improved chemical analysis. The present invention overcomes cost, size or performance limitations of MS, TOF-IMS, FAIMS, and other prior art devices, in novel method and apparatus for chemical species discrimination based on ion mobility in a compact, fieldable packaging. These devices have the further ability to render simultaneous detection of a broad range of species, and have the capability of simultaneous detection of both positive and negative ions in a gas sample. Still further surprising is that this can be achieved in a cost-effective, compact, volume-manufacturable package that can operate in the field with low power requirements and yet it is able to generate definitive data that can fully identify various detected species.

The present invention may be implemented using conventional or advanced manufacturing techniques, such as MEMS or micromachining. These techniques may include, for example, etching of smooth channels, chambers, dams, and intersections, and ports, forming and building upon substrates, etching and bonding, including anodic bonding and fusion, thin film processing and metallization applications, quartz machining, reactive ion etching, high temperature fusion bonding, photolithography, wet etching and the like.

Examples of applications for the present invention include chemical sensors and explosives sensors, and the like. Various modifications of the specific embodiments set forth above are also within the spirit and scope of the invention. For example, it will be further appreciated that embodiments of the invention may be practiced with coaxial, concentric, ring, cylindrical, radial or other features. For example, the electrodes of FIG. 17 may be ring electrodes; as well, structural variations may appear in combination, such as where the electrodes of FIG. 11 are ring electrodes and the remaining layers and electrodes are coaxial and cylindrical, for example.

The examples disclosed herein are shown by way of illustration and not by way of limitation. Although specific features of the invention are shown in some drawings and not in others, this is for convenience only as various features may be combined with any or all of the other features in accordance with the invention.

What is claimed is:

1. A system for analyzing a sample comprising:
a first ion mobility analyzer including:
a flow generator applying a flow generating electric field for moving ions of the sample along a trajectory, and
a time-varying electric field applied to the moving ions for discriminating between ions of the sample.

2. The system of claim 1, wherein the time-varying electric field includes an asymmetric electric field.

3. The system of claim 1, wherein the asymmetric electric field includes a compensation field.

4. The system of claim 1 comprising at least one pair of ion flow generating electrodes for generating the flow generating electric field.

5. The system of claim 4, wherein the electrodes of at least one pair of ion flow generating electrodes are separated by a first flow path associated with the first ion mobility analyzer.

6. The system of claim 5 comprising at least one pair of filter electrodes for generating the time-varying electric field and a compensation field.

7. The system of claim 6, wherein at least one pair of filter electrodes and at least one pair of ion flow generating electrodes are the same pair of electrodes.

8. The system of claim 6, wherein at least one pair of filter electrodes and at least one pair of ion flow generating electrodes are different pairs of electrodes.

9. The system of claim 8, wherein the at least one pair of filter electrodes and at least one pair of ion flow generating electrodes are separated by insulating material.

10. The system of claim 5, wherein a plurality of ion flow generating electrodes are located axially next to each other along the flow path.

11. The system of claim 1, wherein the time-varying electric field is substantially transverse to the flow generating electric field.

12. The system of claim 1 comprising an electronic controller for controlling at least one of the time-varying electric field and the flow generating electric field.

13. The system of claim 12, wherein the controller controls the time-varying electric field and flow generating electric field simultaneously or alternately.

14. The system of claim 1, wherein the flow generating electric field is substantially constant.

15. The system of claim 1, wherein the flow generating electric field is time-varying.

16. The system of claim 5, wherein a portion of the flow path is substantially along a constant axis.

17. The system of claim 5, wherein a portion of the flow path is substantially one of coaxial, concentric, cylindrical, curved, and radial.

18. The system of claim 1, wherein the first ion mobility analyzer includes an ion detector, the ion detector having one or more detector electrodes.

19. The system of claim 1, wherein the first ion mobility analyzer is associated with a first flow path and including a second ion mobility analyzer associated with a second flow path.

20. The system of claim 1 comprising one or more confining electrodes for directing an ion travel path as the ions pass through the system.

21. The system of claim 19 comprising a gas chromatograph for receiving the sample and for eluting constituents of the sample into at least one of the first and second ion mobility analyzers.

22. The system of claim 19 comprising an ion mobility spectrometer (IMS) coupled to an output from at least one of the first and second ion mobility analyzers.

23. The system of claim 1, wherein the first ion mobility analyzer is associated with a first flow path and including a first doping in the flow path.

24. The system of claim 23, comprising a second ion mobility analyzer associated with a second flow path and including a second doping in the second flow path.

25. The system of claim 1 comprising a substrate on which portions of the first ion mobility analyzer are formed.

26. The system of claim 25, wherein portions of the first ion mobility analyzer are formed by one of micromachining, lithography, bonding, metallization, building, fusion, and etching.

27. The system of claim 1, wherein the first ion mobility analyzer is included in an array of ion mobility analyzers, each ion mobility analyzer being associated with a flow path.

28. The system of claim 27, wherein each ion mobility analyzer of the array of ion mobility analyzers includes at least one pair of filter electrodes.

29. The system of claim 27, wherein each ion mobility analyzer of the array of ion mobility analyzers includes at least one pair of ion flow generating electrodes.

30. The system of claim 1 comprising a gas source for flowing a gas in a direction that is substantially opposite to the trajectory of the moving ions.

31. The system of claim 1, wherein the flow generating electric field and time-varying electric field are components of the same electric field.

32. The system of claim 1 comprising a mass spectrometer (MS) coupled to an output from the first ion mobility analyzer.

33. A method for analyzing a sample comprising, generating a flow of ions of the sample using a longitudinal electric field, and directing the flow of ions of the sample through an asymmetric electric field to discriminate between species in the sample.

34. The method of claim 33, wherein the generating is performed by at least one pair of ion flow generating electrodes.

35. The method of claim 34 comprising separating the electrodes of the at least one pair of ion flow generating electrodes using a first flow path.

36. The method of claim 35 comprising generating the asymmetric field and a compensation field using at least one pair of filter electrodes.

37. The method of claim 36, wherein at least one pair of filter electrodes and at least one pair of ion flow generating electrodes are the same pair of electrodes.

38. The method of claim 36, wherein at least one pair of filter electrodes and at least one pair of ion flow generating electrodes are different pairs of electrodes.

39. The method of claim 38 comprising separating the at least one pair of filter electrodes and at least one pair of ion flow generating electrodes using insulating material.

40. The method of claim 35, wherein a plurality of ion flow generating electrodes are located axially next to each other along the first flow path.

41. The method of claim 33, wherein the asymmetric field is substantially transverse to the longitudinal field.

42. The method of claim 33 comprising controlling the longitudinal field and the asymmetric field simultaneously or alternately.

43. The method of claim 33, wherein the longitudinal field is a constant field.

44. The method of claim 33, wherein the longitudinal field is a time-varying field.

45. The method of claim 35, wherein a portion of the flow path is substantially along a constant axis.

46. The method of claim 35, wherein a portion of the flow path is substantially one of coaxial, concentric, cylindrical, curved, and radial.

47. The method of claim 33 comprising detecting the ions using an ion detector, the ion detector having one or more detector electrodes.

48. The method of claim 33, wherein the generating and directing are performed in a first flow path and separate generating and directing are performed in a second flow path.

49. The method of claim 33 comprising directing an ion travel path using at least one confining electrode.

50. The method of claim 48 comprising eluting constituents of the sample from a gas chromatograph into at least one of the first and second flow paths.

51. The method of claim 48 comprising coupling an ion mobility spectrometer (IMS) to an output from at least one of the first and second flow paths.

52. The method of claim 33, wherein the generating and directing are associated with a first flow path and including a first doping in the flow path.

53. The method of claim 52, wherein a separate generating and directing are associated with a second flow path and including a second doping in the second flow path.

54. The method of claim 33, wherein the generating and directing are performed by a first ion mobility analyzer, portion of the first ion mobility analyzer being formed on a substrate.

55. The method of claim 54, wherein portions of the first ion mobility analyzer are formed by one of micromachining, lithography, bonding, metallization, building, fusion, and etching.

56. The method of claim 33, wherein the generating and directing are performed by a first ion mobility analyzer, the first ion mobility analyzer being included in an array of ion mobility analyzers, each ion mobility analyzer being associated with a flow path.

57. The method of claim 56, wherein each ion mobility analyzer of the array of ion mobility analyzers includes at least one pair of filter electrodes.

58. The method of claim 57, wherein each ion mobility analyzer of the array of ion mobility analyzers includes at least one pair of ion flow generating electrodes.

59. The method of claim 33 comprising flowing a gas in a direction substantially opposite to the flow of the ions.

60. The method of claim 33, wherein the longitudinal electric field and asymmetric electric field are components of the same electric field.

61. The method of claim 33 comprising directing a flow of ions exiting the asymmetric field to a mass spectrometer (MS).

* * * * *